(12) United States Patent
Sieber et al.

(10) Patent No.: US 9,169,500 B2
(45) Date of Patent: Oct. 27, 2015

(54) PROCESS FOR THE ENZYMATIC PRODUCTION OF C4 COMPOUNDS FROM C6 SUBSTRATES

(76) Inventors: Volker Sieber, Nandlstadt (DE); André Pick, Bebra-Breitenbach (DE); Broder Rühmann, Straubing (DE)

(*) Notice: Subject to any disclaimer, the term of this patent is extended or adjusted under 35 U.S.C. 154(b) by 0 days.

(21) Appl. No.: 14/006,847

(22) PCT Filed: Mar. 26, 2012

(86) PCT No.: PCT/EP2012/055308
§ 371 (c)(1),
(2), (4) Date: Dec. 9, 2013

(87) PCT Pub. No.: WO2012/127057
PCT Pub. Date: Sep. 27, 2012

(65) Prior Publication Data
US 2014/0171683 A1    Jun. 19, 2014

(30) Foreign Application Priority Data

Mar. 24, 2011   (EP) ..................................... 11159592

(51) Int. Cl.
| | | |
|---|---|---|
| C07C 59/00 | (2006.01) | |
| C12P 7/18 | (2006.01) | |
| C12P 7/16 | (2006.01) | |
| C12P 13/00 | (2006.01) | |

(52) U.S. Cl.
CPC ... *C12P 7/18* (2013.01); *C12P 7/16* (2013.01); *C12P 13/001* (2013.01); *Y02E 50/10* (2013.01)

(58) Field of Classification Search
CPC ........................................................ C12P 7/16
USPC ................................................. 435/14, 25, 26
See application file for complete search history.

(56) References Cited

FOREIGN PATENT DOCUMENTS

| WO | WO-2001/11070 A2 | 2/2001 |
| WO | WO-2010/030711 A2 | 3/2010 |
| WO | WO-2010/076324 A1 | 7/2010 |

OTHER PUBLICATIONS

Niu et al. "Microbial synthesis of the energetic material precursor 1,2,4-butanetriol", J. Am. Chem. Soc., 2003,125:12998-12999.*
Nilegaonkar et al. "Production of 2,3-butanediol from glucose by *Bacillus licheniformis*", World J of Microbiology and Biotechnology, 1992, 8:378-381.*
Ui et al. "Production of L-2,3-butanediol by a new pathway constructed in *Escherichia coli*", Letters in Applied Microbiology, 2004, 39:533-537.*
Yim et al. "Metabolic engineering of *Escherichia coli* for direct production of 1,4-butanediol", 2011, Nature Chemical Biology, 7:445-452.*

Burk "Sustainable production of industrial chemicals from sugars", International Sugar Journal, 2010, 112(1333):30-35.*
Gocke, D. et al., Branched-Chain Keto Acid Decarboxylase from *Lactococcus lactis* (KdcA), a Valuable Thiamine Diphosphate-Dependent Enzyme for Asymmetric C-C Bond Formation, *Advanced Synthesis & Catalysis*, vol. 349, No. 8-9, (Jan. 2007), pp. 1425-1435.
Miller, E.N. etal., Silencing of NADPH-Dependent Oxidoreductase Genes (yqhD and dkgA) in Furfural-Resistant Ethanologenic *Escherichia coli, Applied and Environmental Microbiology*, vol. 25, No. 13 (Jul. 2009), pp. 4315-4323.
Niu, W. et al., Microbial Synthesis of the Energetic Material Precursor 1, 2, 4-Butanetriol, *Journal of the American Chemical Society*, vol. 125, No. 43, (Oct. 2003), pp. 12998-12999.
Yamano, N. et al., Mechanism and Characterization of Polyamide 4 Degradation by *Pseudomonas sp., Journal of Polymers and the Environment; Formerly: Journal of Environmental Polymer Degradation*, vol. 16, No. 2, (May 2008), pp. 141-146.
International Search Report for PCT/EP2012/055308 mailed on Aug. 6, 2012.
Patel, M., et al., "The BREW Project. Medium and Long-term Opportunities and Risks of the Biotechnological Production of Bulk Chemicals from Renewable Resources—The Potential of White Biotechnology", prepared under the European Commission's Growth Programme (DG Research), Final Report, Utrecht University, Sep. 2006, pp. 1-452.
Anastas, P.T. et al., "Through the 12 Principles—Green Engineering", *Environmental Science & Technology*, Mar. 1, 2003, pp. 95-101.
Bechthold, I. et al., "Succinic Acid: A New Platform Chemical for Biobased Polymers from Renewable Resources", Chem. Eng. Technol., 2008, vol. 31, No. 5, pp. 667-654.
Boysen, M.M.K., "Carbohydrates as Synthetic Tools in Organic Chemistry", *Chem. Eur. J.*, 2007, vol. 13, pp. 8648-8659.
Farrell, A.E., "Ethanol Can Contribute to Energy and Environmental Goals", Science, Jan. 27, 2006, vol. 311, pp. 506-508.
Hempel, M., "Novel Process Windows—A Contribution to More Sustainable Chemistry?", *Chem. Eng. Technol.*, 2009, vol. 32, No. 11, pp. 1651-1654.
Morris, D., "The next economy: from dead carbon to living carbon", *J. Sci. Food Agric.*, 2006, vol. 86, pp. 1743-1746.
Schmid, A., et al., "Industrial biocatalysis today and tomorrow", *Nature*, vol. 409, Jan. 11, 2001, pp. 258-268.
Schoemaker, H.E., et al., "Dispelling the Myths—Biocatalysis in Industrial synthesis", *Science*, Mar. 14, 2003, vol. 299, pp. 1694-1697.

* cited by examiner

*Primary Examiner* — Bin Shen
(74) *Attorney, Agent, or Firm* — McCarter & English LLP; Danielle L. Herritt

(57) ABSTRACT

The present invention relates to a novel process for converting a substrate of formula (III) and/or (IV) into a product of formula (I) or (II) comprising the following reactions: a) oxidation of at least one terminal C-atom, b) dehydratation, c) decarboxylation and d) reduction and/or amination. At least step b is enzyme-catalyzed. In a preferred embodiment, all reactions are enzymatically catalyzed. The enzymes catalyzing the reactions are selected from oxidoreductases, decarboxylases, dehydratases and/or aminotransferases. The process may be performed in a cell-free in vitro production system or in an improved fermentative production system.

15 Claims, 23 Drawing Sheets

A.

B.

Purification of Galactose-Oxidase from *Fusarium graminearum*

Purification of Aldehyde-Dehydrogenase from Ovies aries

Purification of Uronate-Dehydrogenase from *Agrobacterium tumefaciens* C58

Purification of Glucarate Dehydratase from *Actionbacillus succinogenes* 130Z

Purification of keto-deoxy-Glucarate Dehydratase from *Acinotebacter baylyi* ADP1

Desalting of Alcohol-Dehydrogenase from *Escherichia coli* K-12

Purification of Alcohol-Dehydrogenase from *Escherichia coli* K-12

PROCESS FOR THE ENZYMATIC PRODUCTION OF C4 COMPOUNDS FROM C6 SUBSTRATES

RELATED APPLICATIONS

This application is a 35 U.S.C. §371 national stage filing of International Application No. PCT/EP2012/055308, filed 26 Mar. 2012, which claims priority to European Patent Application No. 11159592.2, filed 24 Mar. 2011. The entire contents of the foregoing applications are hereby incorporated by reference.

SEQUENCE LISTING

The instant application contains a Sequence Listing which has been submitted electronically in ASCII format and is hereby incorporated by reference in its entirety. Said ASCII copy, created on Apr. 29, 2015, is named 117814-22101_SL.txt and is 20,365 bytes in size.

TECHNICAL FIELD

The present invention relates to a novel process that effectively reduces the functionalization of polyol compounds and comprises the following reactions: a) oxidation of at least one terminal C-atom, b) dehydration, c) decarboxylation and d) reduction and/or amination. At least step b is enzyme-catalyzed. Preferably, all of the reactions may be enzyme-catalyzed combining the activity of 4 types of enzymes: oxidoreductases, e.g. dehydrogenases or oxidases, dehydratases, decarboxylases, and aminotransferases. This inexpensive process can be used to convert hexoses or hexitols into C4-chemicals such as 1,4-butanediol, 1,4-butanedial, 1,4-diaminobutane, 4-hydroxybutyric acid or succinic acid at mild conditions, using only enzymes, water, oxygen (plus an amino donor like ammonium in case of the production of amines) and leaving the inner structure of the carbon chain intact.

BACKGROUND OF THE INVENTION

Climate change and the eventual depletion of the world's fossil raw materials reserves are threatening sustainable development [1, 2]. Renewable resources display a large potential for the substitution of chemical compounds derived from petrochemicals. They allow a more sustainable chemistry with the attempt to design chemical products and processes that reduce or eliminate the use and generation of hazardous substances, minimize waste and energy consumption, favor renewable resources and integrate aspects of recycling [3]. Besides, nature offers a wide range of resources mainly from plants due to fast biomass building with low efforts. At the moment only a few industries are using this immense reservoir of resources [4]. Additionally there have been 12 principles postulated for a Green Engineering concerning new processes or the displacement of antiquated processes to engage in a more sustainable development [5]. Several programs were initiated by the European Union and miscellaneous German institutions that promote the research and development concerning this topic.

Succinic acid is a chemical substance with a broad area of application in the chemical industry. Succinic acid represents an important building block that can be converted into various valuable compounds [6]. Beyond fossil based chemistry, derivatives of succinic acid are announced to have a potential of hundreds of thousands tons [7]. Succinic acid is an intermediate of the TCA cycle (tricarboxylic acid cycle) and one of the fermentation end-products of anaerobic metabolism. The research for biotechnological production processes mainly focused on a whole-cell approach using natural overproducers or recombinant producers. The downstream purification cost for fermentation-based processes normally amounts to more than 60% of the total production costs. For succinic acid purification, the separation of byproducts has a crucial effect on process cost [4].

1,4-Butanediol (BDO) is a four carbon dialcohol that is at the moment manufactured exclusively through various petrochemical routes. BDO represents a chemical building block which can be used for production of gamma-butyrolactone (GBL), tetrahydrofuran (THF), pyrrolidone, N-methylpyrrolidone (NMP) and N-vinyl-pyrrolidone [8]. Presently this family has a market opportunity that exceeds €3.000 M. Approximately 1.4 Mt BDO is produced by chemical catalyst [8]. The demand for BDO stems largely from its use as an intermediate for polybutylene terephthalate (PBT) plastic resins, polyurethane thermoplastics and co-polyester ethers. BDO also serves as a primary precursor to THF, which is employed as an intermediate for poly(tetramethylene glycol) PTMEG copolymers required for lycra and spandex production. Approximately 0.32 Mt of THF is produced globally per year with an annual growth rate over 6%. A significant percentage of growth (>30%) for both BDO and THF is occurring in Asia (China and India). GBL currently is a smaller volume (0.18 M t/year) product which has numerous applications as a solvent, as an additive for inks, paints, and dyes, as well as the primary precursor to pyrrolidone derivatives such as NMP.

However, the replacement of fossil raw materials by biogenic resources is still one of the major obstacles preventing widespread commercialization of such devices.

Enzymes exhibit a great advantage compared to chemical catalysts because they are accepting a wide array of complex molecules as substrates, catalyzing reactions with unparalleled chiral (enantio-) and positional (regio-) selectivities. For this reason, the need of tedious blocking and deblocking steps known in traditional organic synthesis is dispensable [9]. Biological catalysts allow the development of sustainable technologies for the production of chemicals by waste reduction using solvent-free reaction media and minimizing the amount of unrequested by-products complicating the downstream processing [10]. Biocatalyst can be used either as isolated enzymes or in the form of whole cell preparations. The use depends on the requirements of the production process like the half-life of the biocatalyst or the dependency on co-factors. Reaction processes regarding co-factors, especially NAD(P)$^+$, which are utilized in stochimetric quantities whole-cell fermentation is favored. The use of isolated co-factor depending enzymes for establishing a multi-step substrate conversion requires an additional co-factor recycling system for a continuous reaction. Presently, there are some co-factor recycling systems like glucose dehydrogenase/glucose established which allow TTN's (total turnover number) from $10^3$ to $10^6$ or higher for an economical efficient reaction process. It is, however, preferred that cofactor recycling can be achieved without additional substrates.

Carbohydrates represent 95% of the annually renewable biomass. Being renewable carbohydrates such as glucose or other monosaccharides have the potential to compensate the emerging lack of petroleum for the production of bulk chemicals or biofuels. For use as chemicals or fuel carbohydrates contain too many polar functional groups. In the past this was the reason they were disqualified as well-suited precursors for applications in organic chemistry [11]. The use of low molecular weight carbohydrates as well as high molecular weight carbohydrates as the C-source for fermentation processes to produce industrial important chemical compounds is well known. Succinic acid or 2,3-butanediol are two examples of compounds produced by fermentation from carbohydrates. In contrast, the specific conversion of glucose with a multi-step cell free biocatalytic or catalytic process into chemical intermediates is mostly undeveloped. The only economically viable examples are the hydrogenation of glucose to sorbitol followed by the conversion to isosorbide and the oxidation of glucose to gluconate. For the production of C4-compounds from hexoses to date only fermentative processes have been developed, mostly aiming at succinic acid. The Department of Energy of the US has proposed 1,4-diacids, and particularly succinic acid, as key biologically-produced intermediates for the manufacture of the butanediol family of products [6]. However, using fermentation processes, always side products are formed due to the presence of many different enzymes within the organisms. In addition the conditions of the production process (temperature, pH, salt etc.) are limited by the viability of the cells. Product purification often is the most costly process step in a fermentative production system. All these difficulties can be diminished when a cell free production process can be used. By limiting the number of enzymes in such a cell free production to only those essential for the targeted conversion, fewer side products are formed. By applying conditions far from being ambient (e.g. high temperatures, co-solvents) product purification can be more easily integrated into the conversion process. The known pathways from glucose to bifunctional C4-compounds, modified at position 1 and 4, all go via succinate and have never been used in cell free production systems and are probably too difficult to handle (>>10 enzymes) to ever be used in a cell free production system. There is a need for a production process lacking live organisms using just enzymes or other catalysts to cheaply convert hexoses to bifunctional C4 compounds and therefore, there is a need of new and simpler enzymatic pathways, requiring fewer enzymes than existing natural pathways. There is a demand for a new enzymatic pathway that can be applied using purified enzymes or enzymes in cell lysates for a completely cell free in vitro production process or in whole cells containing the enzymes. In addition, it would be beneficial if a new enzymatic pathway could help to improve the yield and productivity of a fermentation process when the enzymes of the pathway are recombinantly expressed in microorganisms.

It is desirable to have such a synthetic pathway for the production of C4 chemicals by alternative means not only to substitute petroleum-based feedstocks but also to facilitate a sustainable process with less waste.

All previously described microbial routes for the production of bifunctional C4-chemicals like 1,4-butanediol or 1,4-aminobutane from C6 polyols and hexoses use more than 10 enzymes in complex metabolic pathways (glycolysis, TCA cycles) requiring a multitude of cofactors (at least $NAD^+$/NADH, ATP/ADP, Coenzyme A) and break down the C6-molecules in two C3-molecules like 3-phospho-glycerate to then reconstruct the C4 entity.

SUMMARY OF THE INVENTION

The present invention provides a novel synthetic enzymatic pathway fulfilling the requirements mentioned above. In the process according to the present invention the carbon chain of the substrate, e.g. a $C_6$ carbon chain, is internally left intact, the functionalities (hydroxyl groups) are moved from the inside of the molecule to the terminal ends and are removed from the molecule by release of the two terminal carbon atoms in the form of $CO_2$. This elegant reaction cascade requires less than ten enzymes and has the potential to be applied in an in vitro enzyme system, and can also be used inside a microbial cell.

The process according to the present invention provides a non-naturally occurring pathway, which for example allows the production of C4-chemicals from hexoses. The resulting chemical compounds can be used for a broad spectrum of industrial applications. It provides a novel route to produce the above mentioned chemicals in a cell-free production system or in an improved fermentative production system.

The invention can be described due to the reactions that are applied: (a) oxidation of a terminal C-atom (alcohol or aldehyde) to carboxylic acid; (b) dehydration of an internal carbon atom to produce a methylen group (deoxy-group) and adjacent to it a carbonyl group; (c) removal of the terminal carboxylic acid by forming carbon dioxide; (d) conversion of a now terminal carbonyl group to a hydroxyl group (reduction), amino group (transamination or reductive amination) or carboxyl group (oxidation).

At least the dehydration reaction is enzymatically catalyzed. In a preferred embodiment, all reactions are enzymatically catalyzed. The enzymes catalyzing the reactions are selected from oxidoreductases, decarboxylases, dehydratases and/or aminotransferases. In a preferred embodiment, the oxidoreductase is an alcohol dehydrogenase, aldehyde dehydrogenase, amino acid dehydrogenase, alcohol oxidase and/or aldehyde oxidase.

During the process, redox reactions take place. To take up and to deliver electrons, a co-factor may be employed. This can be, for example, $NAD^+$/NADH. Alternatively, it is possible to use $NADP^+$/NADPH or $FAD^+$/$FADH_2$ or even other molecules as co-factors for the process; however, it is advantageous that every enzyme can utilize the identical cofactor pair. Preferably, only one free co-factor is employed during the process.

Thus, in an exemplary embodiment, the process can comprise: (a) providing a composition (e.g. mixture) comprising at least one hexose, water, oxygen and when necessary ammonia; (b) providing one (or more) enzymes or catalysts able to oxidize the C1 carbon atom; (c) providing an agent (acid, base, enzyme) for ring-opening of lactones; (d) providing one (or more) enzymes able to oxidize the terminal group at C-6 to generate a diacid compound; (e) providing one (or more) enzymes having a dehydratase activity for deoxygenation of the internal carbon atoms of dihydroxy acids by removal of water; (e) providing one or more agents (acid, base, enzyme) for the decarboxylation of carboxylic acids; (f) providing one (or more) enzymes for the reduction of aldehydes to alcohols or for the oxidation of aldehydes to carboxylic acids or for conversion of aldehydes into amines.

The process of the invention, in its general, basic form or as described in detailed embodiments, can be performed in any convenient manner. Thus, all of the chemical or biochemical reaction steps may be performed in a single reaction vessel. Alternatively, one or more of the reactions may be performed separately. The process may be performed as a batch process or as a continuous process, with products being removed continuously and new substrates being introduced.

Advantageously, the process can be conducted at low to moderate temperatures, such as between 10° C. and 100° C. It is also possible to operate the reaction at temperatures below 10° C. if enzymes from psychrophilic organisms are used. In some embodiments, no external chemical energy source is added, and the only energy added is heat. Preferably, the system is maintained at a constant temperature, taking into consideration that the temperature is a function of substrate concentration, net heats of the reaction and heat losses of the particular system.

Referring to the present invention, the process yield of the different products is typically one mol of product per mol of substrate, in the case that the substrates are monosaccharides or derivates of them.

An exemplary embodiment of the process can contain: (a) glucose as substrate source, water and oxygen (b) one or more enzymes and cofactors capable of oxidizing both terminal carbon atoms to get an aldaric acid (c) dehydrating of the internal carbon atoms (d) decarboxylation for removal of the two terminal C-atoms (e) reduction of the new terminal carbonyl groups to form a diol and (f) oxidation of excess cofactors that are in the reduced form.

A different exemplary embodiment of the process can contain: (a) glucose as substrate source, water and oxygen (b) one or more enzymes and cofactors capable of oxidizing both terminal carbon atoms to get an aldaric acid (c) dehydrating of the internal carbon atoms (d) decarboxylation for removal of the two terminal C-atoms (e) oxidation of the new terminal carbonyl groups to form a diacid and (f) oxidation of excess cofactors that are in the reduced form.

In particular, the oxidation of hexoses at the terminal hydroxylated carbon atom (C-6) can be accomplished by any suitable means, preferably by a chemical or biochemical catalyst. However, more typically, when a biocatalyst is used the oxidation will be in two steps by generating an aldehyde, which is oxidized to a carboxylic acid.

The present invention further provides the alcohol dehydrogenase YjgB from $E.$ $coli$, which may be employed in the process according to the present invention and is capable of catalyzing the conversion of 2,5-dioxopentanoate into 5-hydroxy-2-oxo-pentanoate. This step is depicted in step 6 of FIG. 3. No previously isolated enzyme is capable of catalyzing this reaction.

The present invention also provides an enzyme mixture comprising less than 10 enzymes and optionally cofactors required by the enzymes, wherein the enzymes are selected from oxidoreductases, dehydratases, decarboxylases, and aminotransferases.

DETAILED DESCRIPTION OF EMBODIMENTS OF THE INVENTION

Figure 1:
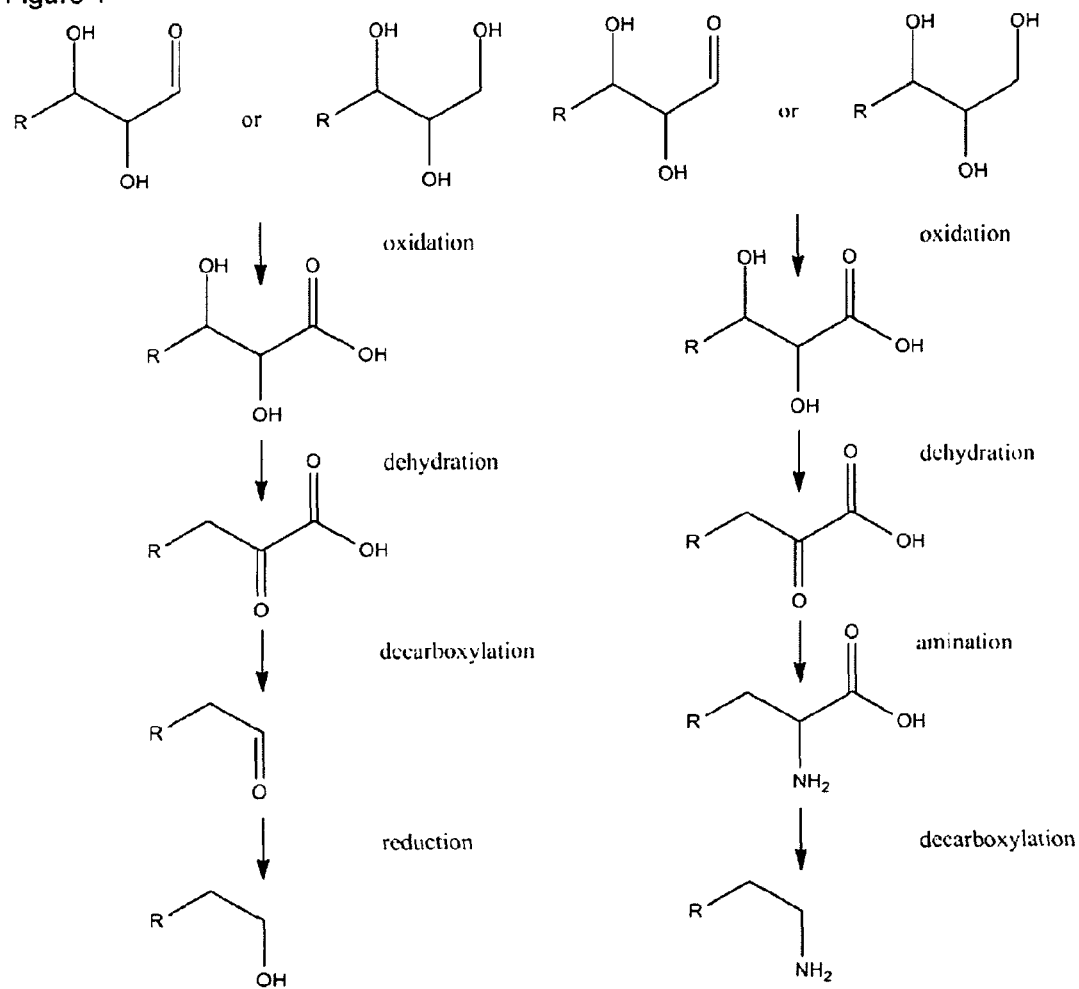
FIG. 1 shows the reaction sequence leading to a reduced number of functional groups of polyols.

The following description provides a detailed discussion of certain embodiments and features of the pathway, co-factor recycling and compositions of the invention. It is not meant to be exhaustive of all such embodiments and features, but rather is presented to give the reader a better understanding of selected exemplary embodiments and features.

To give a better understanding of the invention, certain terms are now defined and for discussed. Terms not discussed or defined herein are to be understood as being used in their normal and customary way in the art. By "hexose" it is meant any monosaccharide as the basic unit of carbohydrates. Hexoses can include allose, altrose, glucose, mannose, gulose, idose, galactose, talose, psicose, fructose, sorbose, tagatose).

C4-chemicals generated in the pathway are described briefly. The term 1,4-butanediol is intended to mean an alcohol derivative of the alkane butane, carrying two hydroxyl groups having the chemical formula $C_4H_{10}O_2$ and a molecular mass of 90.12 g/mol. Succinic acid is a derivative of the alkane butane, carrying two carboxylic acid groups having the chemical formula $C_4H_6O_4$ and a molecular mass of 118.09 g/mol. 1,4-Butanedial is another derivative of the alkane butane, carrying two carbonyl groups having the chemical formula $C_4H_6O_2$ and a molecular mass of 86.09 g/mol. 1,4-Diaminobutane is a derivative of the alkane butane, carrying two amino groups having the chemical formula $C_4H_{12}N_2$ and a molecular mass of 88.15 g/mol.

As used herein, "enzymes" are protein catalysts that catalyze (i.e., accelerate) chemical and biochemical reactions. As used herein "enzyme" is meant to encompass a single enzyme, mixtures comprising one or more enzymes, or enzyme complexes.

The Enzyme Commission number (EC number) is a numerical classification scheme for enzymes, based on the chemical reactions they catalyze. For the purposes of the present invention, an EC number will also be used to specify enzymes. When an enzyme is characterized by an EC number herein, it is understood that there can be multiple enzymes from different sources or organisms that all catalyze the same reaction. The invention is not limited to any particular enzyme or source of enzymes, but rather to certain enzyme-catalyzed reactions in the pathway, as will be described below. The language "an enzyme that is characterized by EC 1.1.1.1", for example, means any amino acid sequence that has the EC number 1.1.1.1 according to at least one art-recognized enzyme information system (such as BRENDA or KEGG) as of the filing date of this application.

As is known in the art, "identity" between two enzymes is determined by comparing the amino acid sequence of one enzyme to the sequence of a second enzyme. Identity may be determined by procedures which are well-known in the art, for example, by utilizing BLAST (Basic Local Alignment Search Tool at the National Center for Biological Information). When enzyme identity is recited in conjunction with an enzyme EC number, according to the present description it is to be understood that there can be many different amino acid sequences that all have the same EC number. Thus, for example, the language "an enzyme that is at least 90% identical to EC 1.1.1.1" means an amino acid sequence that is computed to have 90% or better sequence identity to at least one amino acid sequence that has the EC number 1.1.1.1 according to at least one art-recognized enzyme information system (such as BRENDA or KEGG) as of the filing date of the present application.

The invention is directed to the design of a synthetic pathway to enable the production of different products with isolated enzymes or whole cells in a multi-step enzymatic reaction or in a fermentation process employing microbial cells.

In the process according to the present invention the carbon chain of the substrate, e.g. a $C_6$ carbon chain, is internally left intact, the functional groups are moved from the inside of the molecule to the terminal ends and are removed from the molecule by release of the two terminal carbon atoms in the form of $CO_2$. The process according to the present invention may be employed for the production of bifunctional C4 molecules, e.g. 1,4-butandiol, from C 6 substrates, e.g. hexoses, wherein the bond between the C3 and the C4 is left intact.

In particular, the present invention relates to a process for the conversion of a substrate of the chemical structure (III) and/or (IV) into an alcohol or amine of structure (I) or (II) comprising the following reactions: (a) oxidation of at least one terminal C-atom; (b) dehydration; (c) decarboxylation; (d) reduction and/or amination.

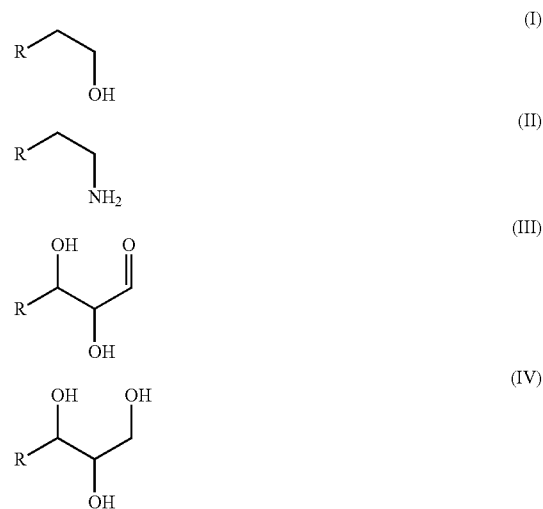

R is a $C_{1-20}$ alkyl, preferably a $C_{1-5}$ alkyl, more preferably a $C_{1-3}$ alkyl, wherein the alkyl may be substituted with one or more hydroxyl groups. Preferably, R may be the following residues but is not limited to these: —$CH_2OH$, —$CH(OH)$—$CH_2(OH)$, —$CH(OH)$—$CH(OH)$—$CH_2(OH)$. In a preferred embodiment of the invention, polyols of the general formula R—$CH(OH)$—$CH(OH)$—$CH_2(OH)$ are used. The substrate may preferably be a C6-polyol, C6-sugar or C6-sugar acid.

At least reaction b is enzyme-catalyzed. In a preferred embodiment, all reactions a-d are enzyme-catalyzed. Reaction a may be catalyzed by an oxidoreductase, reaction b by a dehydratase, reaction c by a decarboxylase and reaction d by an aminotransferase or an oxidoreductase. The oxidoreductase may preferably be an alcohol dehydrogenase, aldehyde dehydrogenase, amino acid dehydrogenase, alcohol oxidase and/or aldehyde oxidase.

The process according to the present invention may be performed in the presence of one or more cofactors for transfer of reduction equivalents. The cofactor(s) may be selected from $NAD^+/NADH$, $NADP^+/NADPH$ and $FAD^+/FADH_2$. Alternatively, $NAD(P)^+/NAD(P)H$-mimicking agents as described in US2003/0022266 may be employed as cofactor.

The production of an alcohol of formula (I) is achieved by the sequence of the following four reactions. These reactions may be performed simultaneously in one reaction mixture (one-pot synthesis) or can also be performed separately in separate reaction vessels.

a) Oxidation (preferably catalyzed by oxidoreductases, EC 1.1.x.x, EC 1.2.x.x), then:
 b) Dehydration (preferably catalyzed by dehydratases, EC 4.2.1.x), after that or simultaneously:
 c) Decarboxylation (catalyzed preferably by decarboxylases, EC 4.1.1.x), then:
 d) Reduction (preferably catalyzed by dehydrogenases, EC 1.1.1.x)

This is illustrated in the following figure (FIG. 1, left).

Reaction a is an oxidation of the terminal hydroxyl function to an aldehyde function. This step may preferably be performed using an oxidase or a dehydrogenase. In the case of using a dehydrogenase, cofactors such as NADP$^+$ or NAD$^+$ are needed. In a further reaction a carboxyl function is generated analogously from the aldehyde function.

Reaction b is a dehydration reaction at two internal hydroxyl functions, resulting in the elimination of water and the generation of a carbonyl function in a-position to the carboxyl function. This reaction is catalyzed by a dehydratase.

Reaction c is a decarboxylation reaction, which leads to a shortening of the carbon chain by one carbon atom by the release of $CO_2$. This reaction may preferably be catalyzed by a decarboxylase that recognizes α-keto carboxylic acids as a substrate. Such a product is formed that contains a terminal carbonyl function (aldehyde).

Reaction d is a reduction of the terminal carbonyl function, preferably using a dehydrogenase. In case this step is catalyzed by a dehydrogenase, cofactors such as NADPH or NADH are needed.

The production of an amine of formula (II) is achieved by the sequence of the following four reactions. These reactions may be performed simultaneously in one reaction mixture (one-pot synthesis) or can also be performed separately in separate reaction vessels.
  a) Oxidation (preferably catalyzed by oxidoreductases, EC 1.1.x.x, EC 1.2.x.x), then:
  b) Dehydration (preferably catalyzed by dehydratases, EC 4.2.1.x), then either:
  c1) Amination (catalyzed preferably by an amino acid dehydrogenases, EC 1.4.x.x or by a transaminases, EC 2.6.1.x), then:
  d1) Decarboxylation (preferably catalyzed by amino acid decarboxylases, EC 4.1.1.x)
  or
  c2) Decarboxylation (preferably catalyzed by α-keto-decarboxylases, EC 4.1.1.x), then:
  d2) Amination (catalyzed preferably by an amino acid dehydrogenases, EC 1.4.x.x or by a transaminases, EC 2.6.1.x)

Reaction a is an oxidation of the terminal hydroxyl function to an aldehyde function. This step may preferably be performed using an oxidase or a dehydrogenase. In the case of using a dehydrogenase cofactors such as NADP$^+$ or NAD$^+$ are needed. In a further reaction a carboxyl function is generated analogously from the aldehyde function.

Reaction b is a dehydration reaction at two internal hydroxyl functions, resulting in the elimination of water and the generation of a carbonyl function in α-position to the carboxyl function. This reaction is catalyzed by a dehydratase.

Reaction c1 is a conversion of a carbonyl function in α-position to a carboxylic acid into an α-amino carboxylic acids preferably using an amino acid dehydrogenase. In case this step is catalyzed by a dehydrogenase, cofactors such as NADPH or NADH are needed. In another preferred embodiment, the conversion of the carbonyl function in α-position to the carboxylic acid into an α-amino carboxylic acids may be achieved via a transaminase and an amino donor, which itself may be regenerated by an amino acid dehydrogenase.

Reaction d1 is a decarboxylation reaction, which leads to a shortening of the carbon chain by one carbon atom by the release of $CO_2$. This reaction may preferably be catalyzed by a decarboxlyase that recognizes α-amino carboxylic acids as a substrate. Finally, a product is formed that contains a terminal amino function.

Reaction c2 is a decarboxylation reaction, which leads to a shortening of the carbon chain by one carbon atom by the release of $CO_2$. This reaction may preferably be catalyzed by a decarboxlyase that recognizes α-keto carboxylic acids as a substrate.

Reaction d2 is a conversion of a terminal carbonyl function into a primary amine preferably using an amin dehydrogenase. In case this step is catalyzed by a dehydrogenase, cofactors such as NADPH or NADH are needed. In another preferred embodiment, the conversion of the carbonyl function in α-position to the carboxylic acid into an α-amino carboxylic acids may be achieved via an ω-transaminase and an amino donor, which itself may be regenerated by an amino acid dehydrogenase. Finally, a product is formed that contains a terminal amino function. This is illustrated by the following figure (FIG. 1, right).

In case the substrate contains several of the structure elements (III) and/or (IV), then the described reaction sequence can occur at all these structure elements. Examples of such molecules include hexoses such as glucose (V) and their alcohol derivatives such as sorbitol (VI):

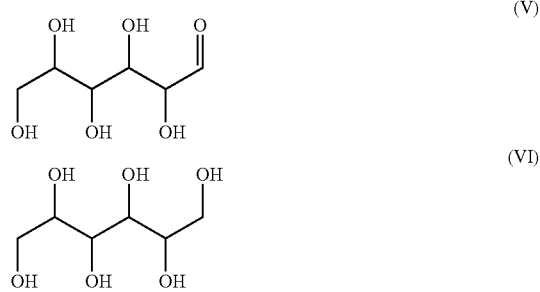

Figure 2:
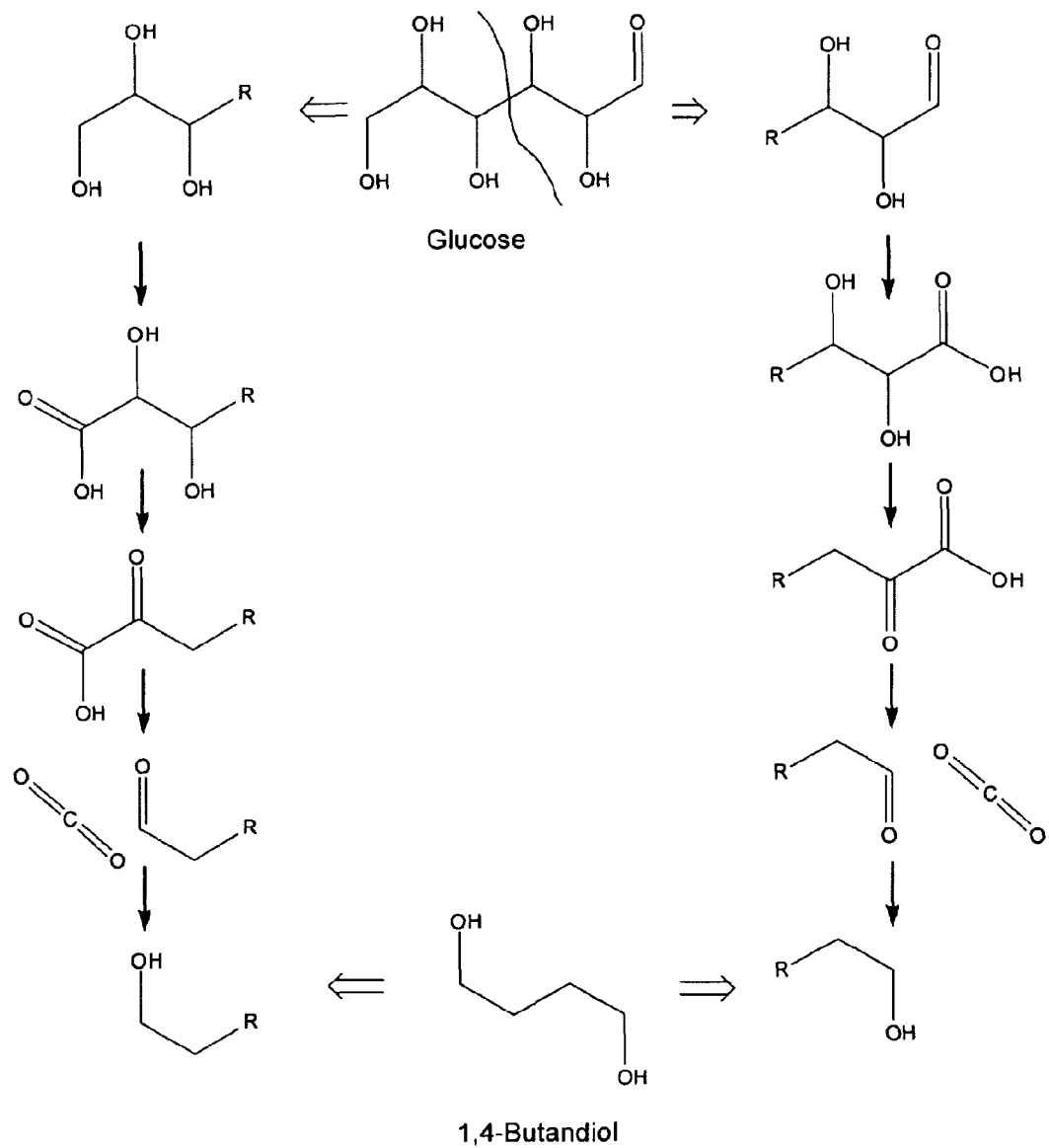
FIG. 2 shows the example for the application of a reaction sequence to convert glucose into 1,4-butandiol.

When these molecules are converted by the described sequence of reactions, 1,4-Butandiol is formed as shown in FIG. 2.

In a preferred embodiment, the present invention therefore relates to an enzymatic/chemical process for the production of bifunctional C4 chemicals from polyols or partially oxidized polyols.

Bifunctional C4 chemicals, such as 1,4-butandiol and 1,4-diaminobutane, are valuable building blocks for producing a wide range of polymers that meet the requirements for a variety of applications.

Polyols are chemical compounds containing at least 4 hydroxyl functions (—OH). Classical chemical methods are not suitable for functionalization or defunctionalization of compounds with several functional groups, since the reactions are not specific and single functional groups cannot be changed selectively.

The precise sequence of reactions at a structural element (III or IV) is exactly defined as described above (oxidation, dehydration, decarboxylation and reduction for the production of alcohols or oxidation, dehydration, amination and decarboxylation or decarboxylation and amination for the production of amines). When two structural units are combined in one substrate, e.g. glucose, the sequence of reactions can proceed in various combinations. Thus, for example with glucose both terminal carbon atoms are first oxidized to the carboxylic acid (formation of glucaric acid), followed by the dehydration at both sides (formation of 2,5-dioxo 3,4 dideoxy glucaric acid), then both are decarboxylated (succinaldehyd) and finally both ends are reduced (1,4 butandiol). Alternatively, glucose could initially be oxidized on one side (C1) (formation of gluconate) followed by the dehydration (2-oxo 3-deoxy gluconate), then followed by the oxidation at the other side of the molecule (C6) (2-oxo 3-deoxy glucaric acid), followed by the decarboxylation and reduction at C1 (2,4-dihydroxy butanoic acid), and finally at the former C6-end dehydration, decarboxylation and reduction take place. These reaction sequences can be presented schematically the following way, for the production of diols:

1.) O1-O6-DH1-DH6-DC1-DC6-R1-R6 (oxidation at C1, oxidation at C6, dehydration at C2 and C3, dehydration at C4 and C5, decarboxylation at C1, decarboxylation at former C6, reduction at former C2, reduction at former C5)
2.) O1-DH1-O6-DC1-R1-DH6-DC6-R6

All together more than 70 different combinations are possible that fall into the constraint presented above, like for example:

3.) O1-DH1-DC1-R1-O6-DH6-DC6-R6
4.) O6-DH6-DC6-R6-O1-DH1-DC1-R1
5.) etc.

The production of 1,4-diaminobutan can analogously be achieved by many different combination of reaction routes.

Figure 3:
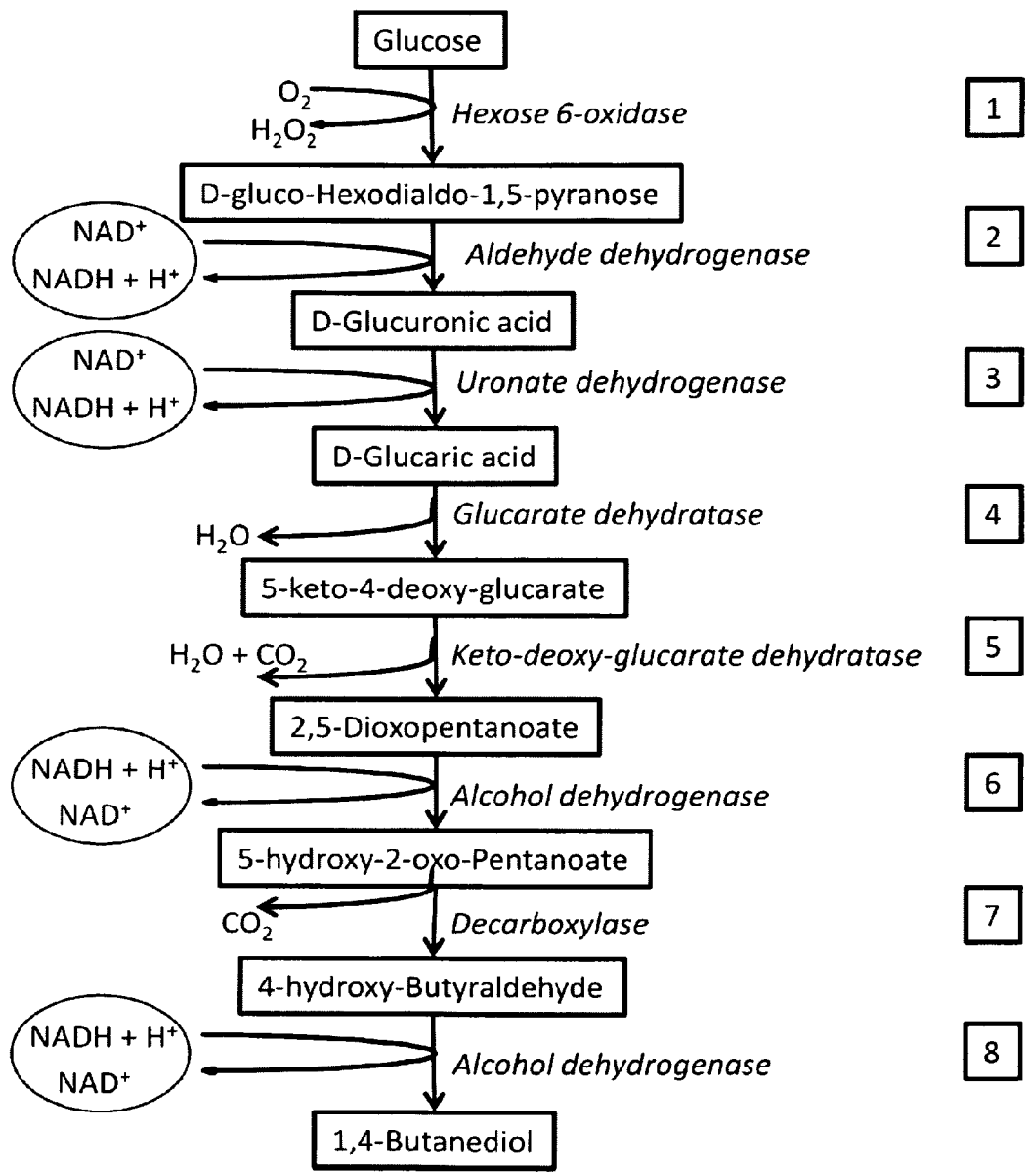
FIG. 3 shows a possible reaction sequence including the different enzymes involved. $NAD^+/NADH$ represent cofactors carrying redox potential. In reality $NADP^+/NADPH$ or $FAD/FADH_2$ could be applied.

In FIG. 3, an example is presented with the successful implementation of the conversion of glucose to 1,4-butanediol. According to the above-described nomenclature this example relates to the order: O1-O6-DH1-DH6-DC6-R6-DC1-R1, wherein O6=reaction 1 and 2, O1=reaction 3, DH6=reaction 4, DH1 and DC6=reaction 5, R6=reaction 6, DC1=reaction 7, R1=reaction 8.

Further embodiments are possible.

In a further embodiment, substrates can be used and introduced at any reaction step in the procedure, for example for the possible use of already oxidized or modified polyols. For example, glucuronic acid can be used as substrate, which reduces the reaction sequence in the above-mentioned embodiment to O1-DH1-DH6-DC6-R6-DC1-R1. When glucaric acid is used, it is reduced to DH1-DH6-DC6-R6-DC1-R1.

The one-pot synthesis can be performed in vitro using isolated or not isolated enzymes, e.g. in enzymes contained in crude cell extracts. Alternatively, the reactions of the process according to the present invention may be performed separately in separate reaction vessels. The reactions may all be carried out separately or they may be individually combined in various combinations. The enzymes used in the reactions may be immobilized, e.g. on a carrier. In another embodiment, the enzymes may be genetically-engineered enzymes or enzyme-complexes, which may preferably exhibit several enzymatic activities. In a further embodiment, the process according to the present invention may be performed in a bioreactor.

The process according to the present invention may also be exploited in microorganisms, wherein the microorganism recombinantly expresses, preferably overexpresses, the enzymes catalyzing the reactions of the process according to the present invention. For example, 1,4 butanediol may be produced from glucose or other hexoses by fermentation or by a whole cell biotransformation. 1,4-butanediol is not a natural metabolite. A synthesis from glucose through this pathway has not yet been demonstrated.

Implementing further enzymatic activities or replacing selected enzymatic activities in the present reaction sequence additional reaction schemes are possible and additional products can be produced (like succinic acid or 4-hydroxy butyric acid). This is shown schematically in FIGS. 4 and 5.

The present invention further provides the alcohol dehydrogenase YjgB from *E. coli*, which is capable of catalyzing the conversion of 2,5-dioxopentanoate into 5-hydroxy-2-oxo-pentanoate. This step is depicted in step 6 of FIG. 3. No previously isolated enzyme is capable of catalyzing this reaction. In Example 2.6, the production and characterization of this enzyme is described.

The alcohol dehydrogenase YjgB from *E. coli* may be used in the process according to the present invention.

The present invention also provides an enzyme mixture comprising less than 10 enzymes and optionally cofactors required by the enzymes, wherein the enzymes are selected from oxidoreductases, dehydratases, decarboxylases, and aminotransferases. The oxidoreductase may preferably be an alcohol dehydrogenase, aldehyde dehydrogenase, amino acid dehydrogenase, alcohol oxidase and/or aldehyde oxidase.

Said enzyme mixture may be used in the process according to the present invention.

The enzyme mixture according to the present invention may comprise one or more cofactors for transfer of reduction equivalents. The cofactor(s) may be selected from $NAD^+/NADH$, $NADP^+/NADPH$ and $FAD^+/FADH_2$. Alternatively, $NAD(P)^+/NAD(P)H$-mimicking agents as described in US2003/0022266 may be employed as cofactor.

Exemplary enzymes suitable for use in the process according to the present invention are listed in table 1. They provide possible solutions and are described in the following paragraphs as particular embodiments for a better understanding. The replacement of individual enzymes or more is within the skill of an ordinary artisan.

TABELLE 1

Exemplary list of enzymes for the embodiments discussed in the text and FIGURES

Enzymes and Catalysed Reactions

| EC | Enzyme Name | Reaction |
|---|---|---|
| 1.1.3.9 | Hexose-6-oxidase | D-glucopyranose + $O_2$ ⇌ D-gluco-dialdose + $H_2O_2$ |
| 1.1.3.4 | Glucose oxidase | D-glucopyranose + $O_2$ ⇌ D-glucono-1,5-lactone + $H_2O_2$ |
| 1.1.1.118 | Glucose dehydrogenase | D-glucopyranose + $NAD^+$ ⇌ D-glucono-1,5-lactone + NADH |
| 4.2.1.39 | Gluconate dehydratase | D-gluconate ⇌ 2-keto-3-deoxy-D-gluconate + $H_2O$ |
| 1.1.1.126 | 2-keto-3-deoxy-D-gluconate-6-dehydrogenase | 2-keto-3-deoxy-D-gluconate + $NAD^+$ ⇌ 4,5-dihydroxy-2,6-dioxohexanoate + NADH |
| 1.2.1.3 | Aldehyde dehydrogenase | D-glucopyranose + $NAD^+$ + $H_2O$ ⇌ D-glucuronic acid + NADH |
| 1.1.1.203 | Uronate dehydrogenase | D-gluco-dialdose + $NAD^+$ + $H_2O$ ⇌ D-glucuronic acid + NADH<br>D-glucuronate + $NAD^+$ + $H_2O$ ⇌ D-glucaric acid + NADH |

TABELLE 1-continued

Exemplary list of enzymes for the embodiments discussed in the text and FIGURES

Enzymes and Catalysed Reactions

| EC | Enzyme Name | Reaction |
|---|---|---|
| 4.2.1.40 | Glucarate dehydratase | D-glucaric acid ⇌ 5-dehydro-4-deoxy-D-glucarate + $H_2O$ |
| 4.2.1.41 | Keto-deoxy-glucarate dehydratase | 5-dehydro-4-deoxy-D-glucarate ⇌ 2,5-dioxopentanoate + $H_2O$ + $CO_2$ |
| 4.1.1.1 | Pyruvate decarboxylase | 2,5-dioxopentanoate ⇌ succinaldehyde + $CO_2$ |
| 4.1.1.72 | branched-chain-2-oxoacid decarboxylase | 2,5-dioxopentanoate ⇌ succinaldehyde + $CO_2$ |
| 1.1.1.1 | Alcohol dehydrogenase | succinaldehyde + 2 NADH ⇌ 1,4-butanediol + 2 $NAD^+$ + 2 $H_2O$ |
| 1.4.99.3 | Amine dehydrogenase | succinaldehyde + 2 NADH + 2 $H^+$ + 2 $NH_3$ ⇌ 1,4-diaminobutane + 2 $NAD^+$ + 2 $H_2O$ |
| 2.6.1.18 | Transaminase | succinaldehyde + 2 L-alanine ⇌ 1,4-diaminobutane + 2 pyruvate |

In the following, a detailed description of single conversion steps within the scope of this invention is given. The following paragraphs will describe illustrative enzyme selections that demonstrate one or more embodiments of the invention.

Initially the oxidation of the C-6 is achieved with hexose-6-oxidase (Eq. 1) followed by the oxidation of the C-1 carbon to a carboxylic group (Eq. 2) using uronate dehydrogenase (EC 1.1.1.203). This step requires a ring-opening (lactone hydrolysis) which could be achieved by acid/base catalysis, enzymes or other ways.

$$C_6H_{12}O_6+O_2 \rightleftharpoons C_6H_{10}O_6+H_2O_2 \qquad [\text{Eq. 1}]$$

$$C_6H_{10}O_6+NAD^++H_2O \rightleftharpoons C_6H_{10}O_7+NADH+H^+ \qquad [\text{Eq. 2}]$$

As an alternative route it is possible to use an aldehyde dehydrogenase (Eq. 3) (EC 1.2.1.3) for the oxidation of the C-6. Using aldehyde dehydrogenase the C-1 carbonyl group is simultaneously oxidized to the carboxyl group.

$$C_6H_{12}O_6+2NAD^++H_2O \rightleftharpoons C_6H_{10}O_7+2NADH+2H^+ \qquad [\text{Eq. 3}]$$

To achieve the complete oxidation of both terminal carbon atoms the uronate dehydro-genase (EC 1.1.1.203) catalyzes in a second step the oxidation of the aldehyde group at C-6 to the corresponding carboxylic group (Eq. 4).

$$C_6H_{10}O_7+NAD^++H_2O \rightleftharpoons C_6H_{10}O_8+NADH+H^+ \qquad [\text{Eq. 4}]$$

The next step is the defunctionalization (deoxygenation) of the internal carbons. Removal of the hydroxyl group at position C-4 is achieved by using the enzyme glucarate dehydratase (EC 4.2.1.40) or other suitable dihydroxy acid dehydratase. After the elimination of water a rearrangement at position C-5 ("keto-enol-tautomerie") occurs leading to a carbonyl group at position C-5 (Eq. 5) and a methylen-group at C4.

$$C_6H_{10}O_8 \rightleftharpoons C_6H_8O_7+H_2O \qquad [\text{Eq. 5}]$$

An additional dehydration is achieved by keto-deoxy-glucarate dehydratase (EC 4.2.1.41) which not only catalyzes the dehydration of the substrate but also a first decarboxylation (Eq. 6). The product is a C-5 compound.

$$C_6H_8O_7 \rightleftharpoons C_5H_6O_4+H_2O+CO_2 \qquad [\text{Eq. 6}]$$

When $CO_2$ is continuously removed from liquid reaction solution, the net reaction becomes favorable (in the forward direction) according to Le Chatelier's principle. Therefore, it is preferable to remove the gaseous products as it is formed.

For the production of C-4 compounds a further enzymatic step is required. Using a decarboxylase (EC 4.1.1.x) the other carboxyl group is removed as carbon dioxide (Eq. 7).

$$C_5H_6O_4 \rightleftharpoons C_4H_6O_2+CO_2 \qquad [\text{Eq. 7}]$$

If the desired product is 1,4-butanediol both carbonyl groups are reduced to hydroxyl groups (Eq. 8).

$$C_4H_6O_2+2NADH+2H^+ \rightleftharpoons C_4H_{10}O_2+2NAD^+ \qquad [\text{Eq. 8}]$$

If the desired product is succinic acid both carbonyl groups are oxidized to carboxyl groups (Eq. 9).

$$C_4H_6O_2+2NAD^++2H_2O \rightleftharpoons C_4H_6O_4+2NADH+2H^+ \qquad [\text{Eq. 9}]$$

If the desired product is 4-Hydroxybutyric acid one carbonyl group is reduced to a hydroxyl group and the other carbonyl group is oxidized to a carboxyl group (Eq. 10).

$$C_4H_6O_2+H_2O \rightleftharpoons C_4H_8O_3 \qquad [\text{Eq. 10}]$$

If the desired product is 1,4 diaminobutane both carbonyl groups are reduced to amino groups. This step can be done by different enzymes, e.g. amine dehydrogenase (Eq. 11) (EC 1.4.99.3) or transaminase (Eq. 12) (2.6.1.18).

$$C_4H_6O_2+2NADH+2H^++2NH_3 \rightleftharpoons C_4H_{12}N_2+2NAD^++2H_2O \qquad [\text{Eq. 11}]$$

$$C_4H_6O_2+2R-NH_2 \rightleftharpoons C_4H_{12}N_2+2R=O \qquad [\text{Eq. 12}]$$

In another example the conversion of glucose is initiated by the oxidation of C-1 by glucose dehydrogenase (Eq. 13) (EC 1.1.1.118) or glucose oxidase (Eq. 14) (EC 1.1.3.4) to yield gluconolactone, which is hydrolyzed to gluconate.

$$C_6H_{12}O_6+NAD^+ \rightleftharpoons C_6H_{10}O_6+NADH+H^+ \qquad [\text{Eq. 13}]$$

$$C_6H_{12}O_6+O_2 \rightleftharpoons C_6H_{10}O_6+H_2O_2 \qquad [\text{Eq. 14}]$$

The oxidation of C-1 is followed by the dehydration using gluconate dehydratase (Eq. 15) (EC 4.2.1.39).

$$C_6H_{12}O_7 \rightleftharpoons C_6H_{10}O_6+H_2O \qquad [\text{Eq. 15}]$$

Subsequently, the oxidation of C-6 of 2-keto-3-deoxy-gluconate is achieved using 2-keto-3-deoxy-gluconate 6-dehydrogenase (Eq. 16) (EC 1.1.1.126). Alternatively, 2-keto-3-deoxy-gluconate can also first be decarboxylated using a decarboxylase.

$$C_6H_{10}O_6+NAD^+ \rightleftharpoons C_6H_8O_6+NADH+H^+ \qquad [\text{Eq. 16}]$$

The enzymatic process for the conversion of hexoses, like glucose, may be summarized into three main steps as follows:

(a) the oxidation of the terminal carbon atoms and their/its removal as carbon dioxide; (b) removal of the hydroxyl-groups at position 3 and 4; (c) the conversion of the terminal carbonyl groups into the desired functionality by oxidation, reduction or transfunctionalization.

In a preferred embodiment these three main steps are catalyzed by in total only four different enzymes (e.g. aldehyde dehydrogenase, alcohole dehydrogenase, dihydroxy acid dehydratase, decarboxylase) having substrate specificities wide enough to be active on both sides of the C6, C5 or C4 chemical.

Figure 4:
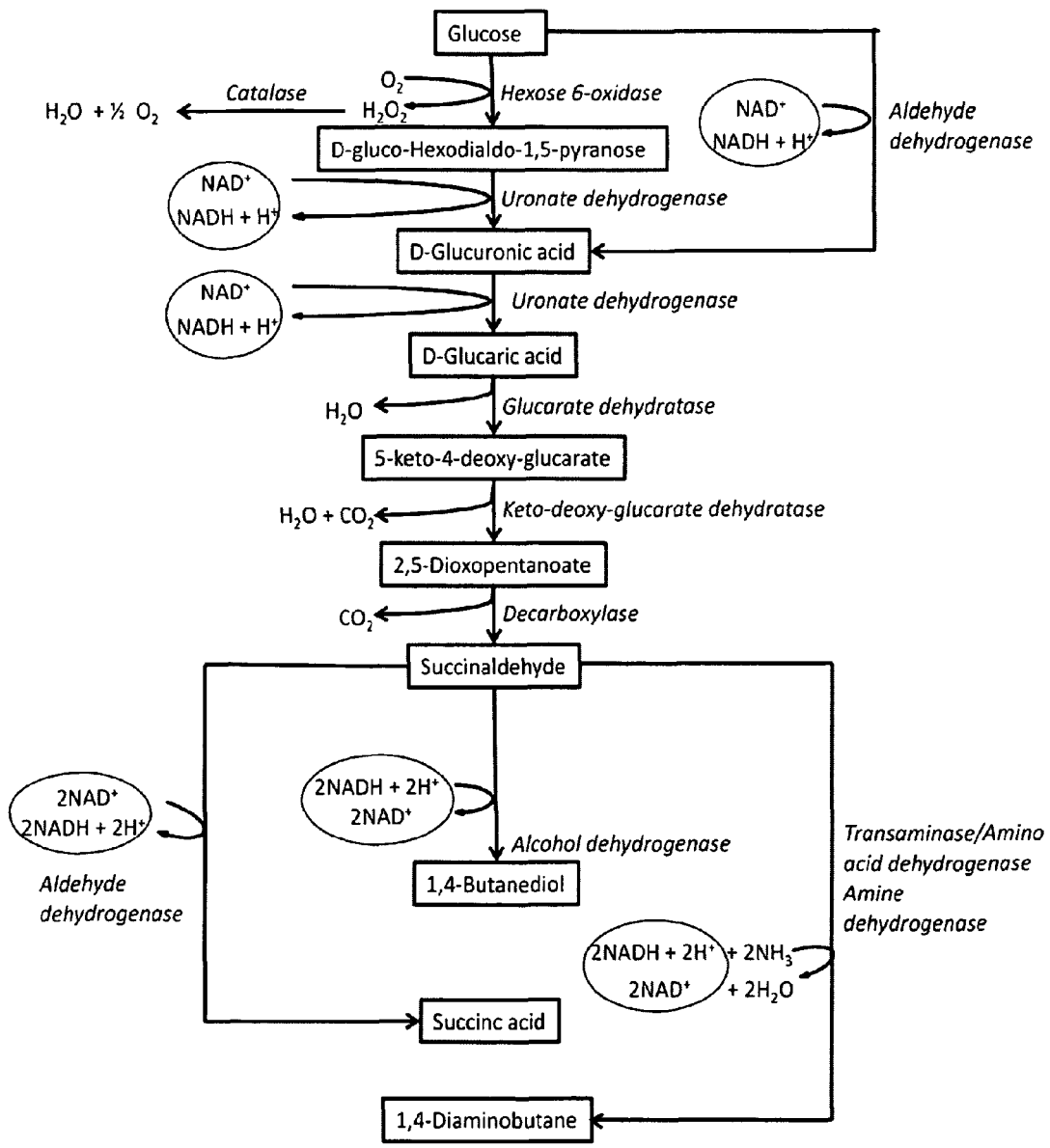
FIG. 4 is a schematic diagram showing one possible synthetic pathway for converting hexoses into different possible products starting with the oxidation at position C-6. Solid black arrows show the different enzymatic steps. Circles illustrate the co-factor recycling system which depends on the produced product. The NADH production per mol glucose depends on the enzymes used.
Figure 5:
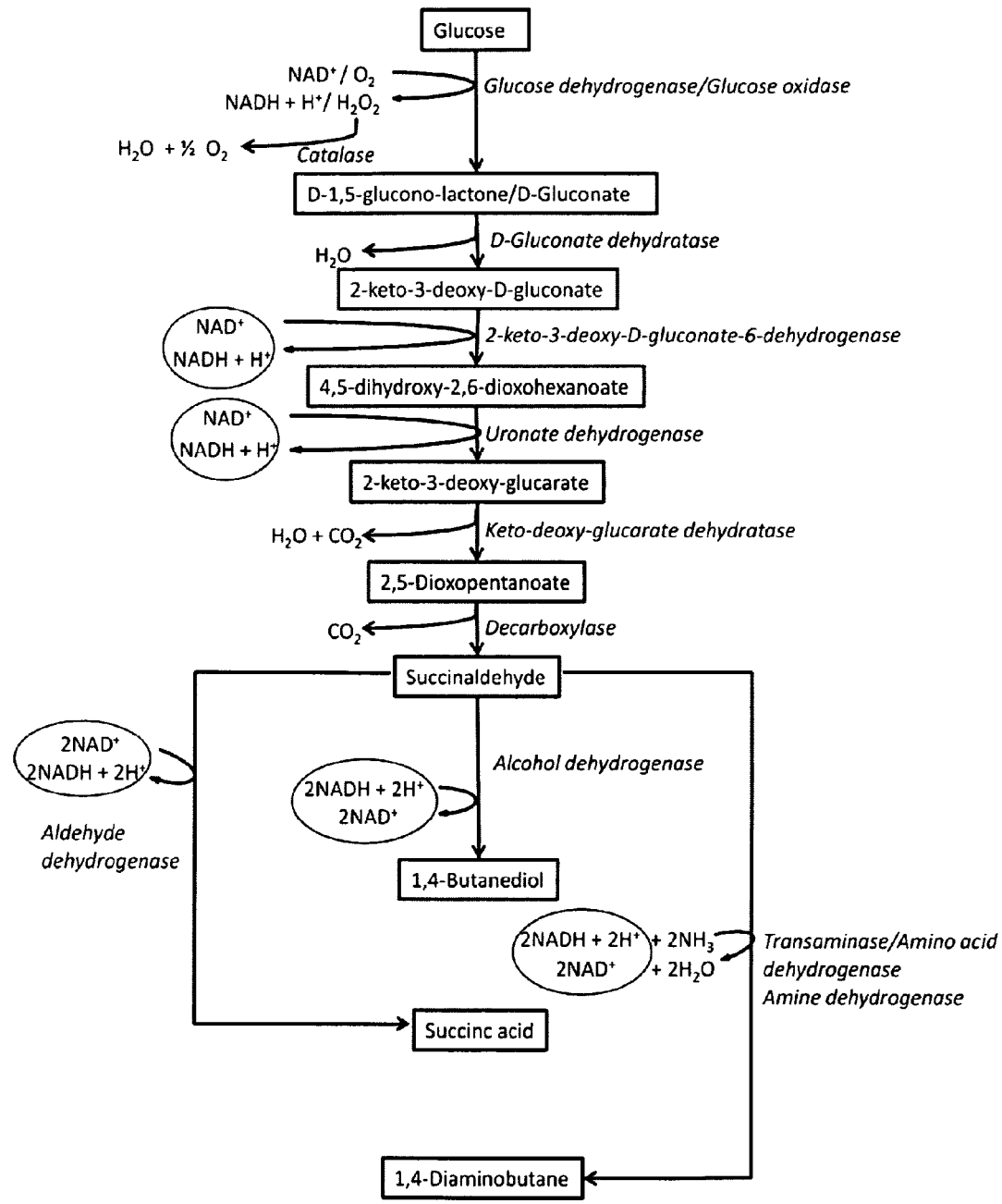
FIG. 5 shows a synthetic pathway for converting hexoses into different possible products starting with the oxidation at position C-1. Solid black arrows show the different enzymatic steps. Circles illustrate the co-factor recycling system which depends on the produced product. The NADH production per mol glucose depends on the enzymes used.

In general, selection of a plurality of enzymes that lead to glucaric acid is within the skill of an ordinary artisan. One particular embodiment is discussed in this invention using glucose as starting substrate (FIG. 4, FIG. 5 and Table 1). Other embodiments employ similar enzymes, such as enzymes with at least 80% preferably at least 90% sequence identity to the enzymes listed in Table 1.

In some embodiments, enzymes are added directly together with the required co-factors into the aqueous solution of substrate(s). The quantity of enzymes to add depends on the desired reaction temperature and residence time and the determination of optimal enzyme quantity or concentration lies within the ordinary skill of the person skilled in the art. In general, there will be concentration of each particular enzyme above which no further enhancement in reaction rate occurs. The optimal quantity of enzyme will be dictated by overall economics.

The enzymes may be purified (but are not necessarily purified), and they can exist in the form of mixtures of enzymes or enzyme complexes with the desired functions. Enzymes can be added in the form of lysed cells which produced the enzymes in a previous fermentation process. In this case, there could also be cell fragments added to the reactor.

The advantage of using a cell-free system is that no unwanted side-reactions occur. The co-factor ($NAD^+$) is continuously recycled in the system. That is, these substances are produced and consumed in equal rates. Preferably, it is possible to use a co-factor recycling system, e.g. NADH Oxidase, for the generating $NAD^+$ (Eq. 17) in case that excess NADH is developed during the reaction cascade.

$$NADH + H^+ + O_2 \leftrightarrows NAD^+ + H_2O_2 \quad [\text{Eq. 17}]$$

If necessary, accumulated hydrogen peroxide can be efficiently eliminated by catalase (Eq. 18).

$$2H_2O_2 \leftrightarrows O_2 + 2H_2O \quad [\text{Eq. 18}]$$

By the use of close to irreversible reactions, like decarboxylation, the equilibrium of the process is continuously shifted to the desired end product.

In another embodiment the enzymes are expressed recombinantly in a suitable microorganism and the conversion of the substrate is achieved using whole cell catalysis or in a fermentation process.

The disadvantage of using a fermentation process for generation of chemical compounds lies in the difficult downstream product purification. The separation of byproducts has a crucial effect on process costs. In a cell-free production system using isolated enzymes only those reactions are catalyzed that lead to the desired intermediates and final products and the amount of byproducts is reduced drastically.

The pH of the solution is not regarded as particularly critical, but pH will impact activity of each enzyme in a potentially different way. A person of ordinary skill in the art can readily perform routine experimentation, given a specific selection of enzymes, to determine the optimum pH, or to determine a range of preferred pH values, with respect to product yield and production rate. In other words, the process of invention can comprise adjusting one or more parameters during the reaction to maintain parameter or optimize parameter. An illustrative range of preferred pH values for some embodiments is pH 2-12, more preferably 4-9, and most preferably a neutral pH, such as pH 6-8.

Temperature is not regarded as being critical to the present invention. Low to moderate temperatures are appropriate, especially when mesophilic enzymes are chosen. The process can generally be practiced conveniently at one or more temperatures from 10° C. to about 100° C., enzymes selected will have its own respective function of the specific enzymes chosen. One skilled in the art will recognize that temperatures outside the range of 10° C. to 100° C. could even be employed, such as when thermophilic or psychrophilic enzymes are selected. In some embodiments, no external energy is added, and the temperature will be a function of substrate concentration, net heats of reactions and heat losses in the system.

Sources of enzymes can be any organism in which the enzyme (encoded gene product) is capable of catalyzing the referenced reaction. Including both prokaryotic and eukaryotic organisms, this includes, but is not limited to, bacteria like archaea and eubacteria and eukaryotes like yeast, plant, insects, animal and mammal. The recombinant expression or natural expression of the enzyme can be applied to different kinds of expression systems.

Pressure is also not critical to the present invention, but a skilled artisan will appreciate that the reaction pressure can impact the equilibrium distribution of species. A high pressure, such as several atmospheres, would tend to inhibit as the $CO_2$ should be removed.

The process can be conducted in a batch reactor, continuous reactor, membrane reactor or combination of these. A variety of means for agitation (mixing) can be employed, or plug-flow reactor without internal mixing can be effective. Unconverted reactants can be recycled to the reactor inlet, as in known in the art.

Optimization can also be carried out to improve the overall reaction rate the stability of some or all of the enzymes. Such optimization can include, for example, enzyme component optimization via metabolic engineering and modeling; substitution of mesophilic enzymes by recombinant thermophilic or even hyperthermophilic enzymes; protein engineering to improve enzyme activity and/or selectivity; higher concentrations of enzymes and substrates; variation of process parameters such as pH and temperature; stabilization of enzymes through additives; enzyme immobilization; and development of minimal microorganism to create an in vivo enzyme system that produces the different products. It is within the ordinary skill of the person skilled in the enzyme art to conduct such optimization, and the present invention is intended to include this type of experimentation. Statistical experimental design can be employed to explore global response surfaces and establish models of product yield and rate versus process and enzyme factors as well as interaction effects.

In yet another embodiment of this invention pentoses are used instead of hexoses for example for the production of 1,2,4-butantriol using the same mechanism of a) oxidation of terminal C1, b) dehydration of internal C3, c) decarboxylation of C1 and d) reduction of C2.

The present invention is not limited in scope by specific embodiments described herein. Indeed, various modifications of the invention in addition to those described herein will become apparent to those skilled in the art in view of the

EXAMPLES

Example 1

Enzymatic Production of 1,4-butandiole

The genes encoding the following enzymes were cloned from their host or synthesized and recombinantly expressed in E. coli.

| Component | Concentration stock solution | Sample | Concentration in test |
|---|---|---|---|
| Uronate-Dehydro-genase (Udh) | 300 U/ml | 11.79 μl | 3.75 U |
| Glucarate-Dehydratase (GlucD) | 289 U/ml | 13 μl | 3.75 U |
| Keto-deoxy-Glucarate-Dehydratase (KdgD) | 32 U/ml | 117.2 μl | 3.75 U |
| Alcohol Dehydrogenase (YjgB) | 1.7 U/ml | 1000 μl | 1.7 U |
| Decarboxylase (KdcA) | 75 U/mg | 5 mg | 375 U |
| Alcohol Dehydrogenase (YqhD) | | 2000 μl | N.a. |
| $NAD^+$ | 100 mM | 1000 μl | 10 mM |
| NADPH | 50 mM | 500 μl | 2.5 mM |
| Na-Glucuronate | 500 mM | 400 μl | 20 mM |
| Buffer | | 4958.01 μl | |
| Total Volume | | 10.000 μl | |

Buffer-Content:
100 mM HEPES/NaOH pH 7.5
100 mM NaCl
5 mM $MgCl_2$
0.1 mM TPP
10% Glycerol $NAD^+$ was dissolved in assay-buffer and the pH was adjusted to 6.5 to prevent fluctuations during the test. Na-glucuronate was dissolved as a stock solution with a concentration of 500 mM in the assay buffer. The enzymes were taken from glycerol stocks: Uronate dehydrogenase *A. tumefaciens* C58, *E. coli* dehydrogenase YjgB and *E. coli* dehydrogenase YqhD (25% glycerol, 25 mM Tris-HCl pH 8.0), glucarate dehydratase *A. succinogenes* 130Z and keto-deoxy-glucarate dehydratase *A. baylyi* ADP1 (27.5% glycerol, 25 mM Tris-HCl pH 8.0, 25 mM NaCl, 0.5 mM DTT).

Figure 6:
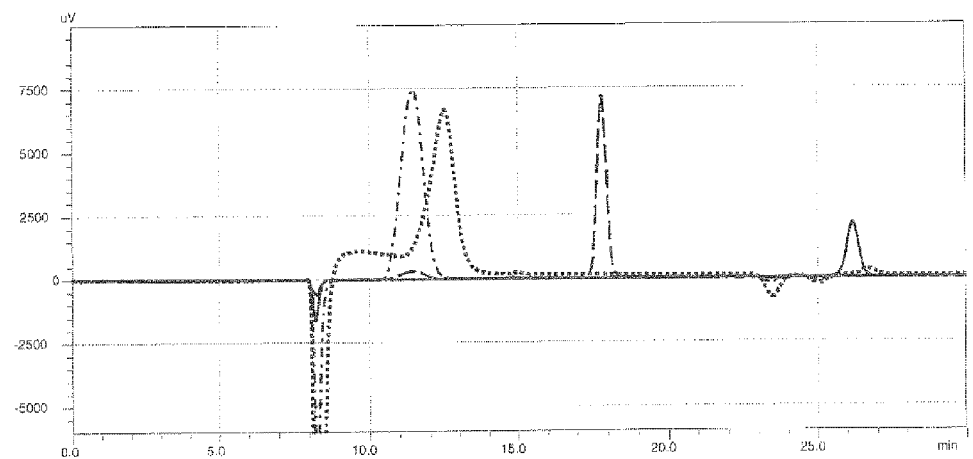
FIG. 6 shows chromatograms representing the results of Example 1. A. Standards, Solid line=1,4-Butandiole, retention time at 26.2 min, Dashed line=keto-deoxy Glucarate, Dotted line=Glucarate, Dashed-dotted line=NADH; B. Sample containing all enzymes after 24 h. The peak at 26.2 min retention time indicates the formation of 1,4-butandiole.
Figure 6:
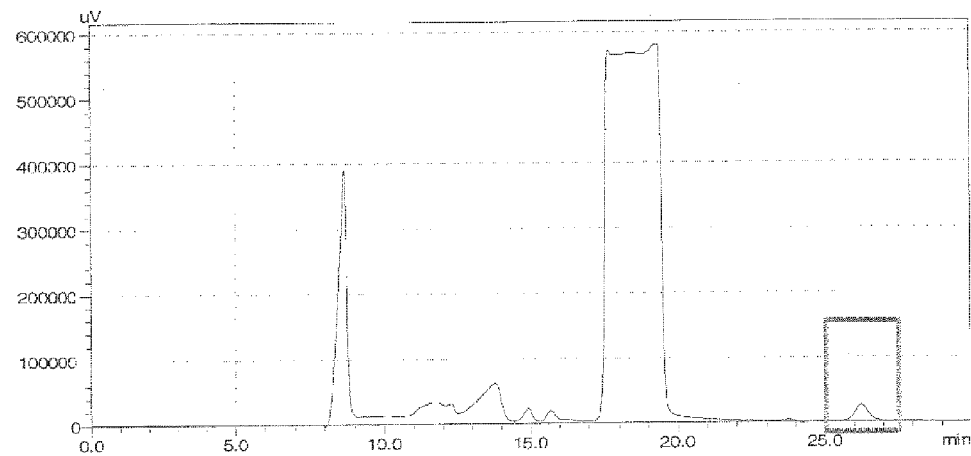

The required amount of NADPH was weighed, dissolved directly in buffer and added to the reaction mixture. The decarboxylase KdcA from *L. lactis* was directly weighed as lyophilisate and added. The test mixture was incubated for 24 h at 30° C. After 24 h samples (sample volume 500 μl) were taken and analyzed by HPLC for the enzymatic reaction. The results are shown in the chromatograms in FIG. 6. The peak at 26.2 min retention time in FIG. 6 B indicates the formation of 1,4-butandiole. According to the peak area more than 2 mM 1,4-Butanediol was produced.

Example 2

Enzyme Preparation and Activity Tests 2.1 Galactose-Oxidase from *Fusarium graminearum* (GaoA-M-RQWY)

The gene gaoA-M-RQWY for the enzyme galactose-oxidase from *Fusarium graminearum* was a synthetic gene codon-optimized for expression in *Escherichia coli*. It was cloned into a derivative of pET28a with an alternative MCS carrying additionally the recognition sites for the two restriction-endonucleases BsaI and BfuAI.

The enzyme expression was done with an autoinduction-media developed by F. W. Studier and colleagues. The method is based upon a buffered medium that contains a mixture of carbon sources, including lactose. The medium allows the recombinant protein expression without any additional inducer substances. In the following section the reagents and stock solutions are described: ZY, 20×NPS, 50×5052, $MgSO_4$, Antibiotic.

ZY
10 g tryptone
5 g yeast extract
925 ml water
20×NPS

| Component | 1 liter | mol/liter |
|---|---|---|
| dd $H_2O$ | — | |
| $(NH_4)_2SO_4$ | 66 g | 0.5M |
| $KH_2PO_4$ | 136 g | 1M |
| $Na_2HPO_4$ | 142 g | 1M |

50×5052

| Component | 1 liter |
|---|---|
| Glycerol (weigh in beaker) | 250 g |
| $H_2O$ | 730 ml |
| Glucose | 25 g |
| α-Lactose | 100 g |

1 M $MgSO_4$
24.65 g $MgSO_4.7H_2O$
Water to make 100 ml
ZYP-5052 Rich Medium for Auto-Induction
Add 1 M $MgSO_4$ before adding 20×NPS to avoid precipitate
Kanamycin is used at significantly higher concentrations (100 μg/ml) than is normally (25-40 μg/ml). Studier has found that in the T7 expression strains in these rich media, it does not provide adequate selection at the lower concentration

| Component | 200 ml |
|---|---|
| ZY | 186 ml |
| 1M $MgSO_4$ | 0.2 ml |
| 50× 5052 | 4 ml |
| 20× NPS | 10 ml |
| Kanamycin (30 mg/ml) | 0.667 ml |

The plasmid pCBR-NH-gaoA-M-RQWY-F.g. carrying the galactose-oxidase from *Fusarium graminearum* was used to transform *E. coli* BL21 (DE3) for use for protein expression. The recombinant *E. coli* BL21 strain was cultivated in auto-induction media described above with the following procedure. First, the bacteria culture was cultivated at 37° C. and 150 rpm for 3 h, after that the culture was transferred to 16° C. at 150 rpm for additionally 21 h.

Figure 7:
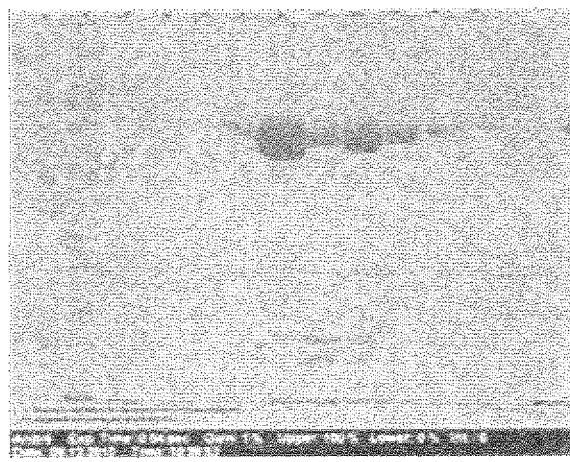
FIG. 7 shows the analysis of the product of the purification of galactose oxidase from $Fusarium$ $graminearum$.

After centrifugation, cells were frozen or directly used and suspended in Lysis/Wash Buffer (50 mM phosphate, pH 8.0, 500 mM NaCl, 10% glycerol, 20 mM imidazole) and for that 1 g of cells were resuspended in 10 ml Buffer. For cell disruption a cell-disrupter was used. After this step 10 µl DNase Stock-Solution (10 mg/ml DNase) per 10 ml and 25 µl of 1 M MgSO$_4$ were added and incubated for 20 min at room temperature for DNA cleavage. After centrifugation 45 min at 40.000 g at 4° C. to clarify the cell extract, the supernatant was loaded on a 5 ml HisTrap FF column (GE Health Care Europe) using a Äkta Purifier 100 (GE Health Care Europe). After sample loading, the column was washed with 5 volumes of Lysis/Wash Buffer and the protein was eluted with the same buffer containing 500 mM imidazole. In the final step the buffer exchange was done using a HiPrep26/10 desalting column (GE Health Care Europe) with a mobile phase composed of 100 mM NaPi, pH 7.0. After this the protein was tested in an activity assay and stored at −20° C. The analysis of the product is shown in FIG. 7.

Enzyme activity on glucose as substrate of the purified enzyme was measured with a coupled assay using horse radish peroxidase and ABTS at 445 nm at 25° C. The assay was done in 96-well microtiter plates containing the following components:

| Component | Assay conc. | Unit | Stock solution conc. | Unit | Stock solution pro well (µl) |
|---|---|---|---|---|---|
| NaPi (pH 7.0) | 50.00 | mM | 500.0 | mM | 20.00 |
| Glucose | 250.0 | mM | 1000.0 | mM | 50.00 |
| Catalase | 850 | U/ml | 609131.0 | mM | 0.28 |
| Cu$_2$SO$_4$ | 0.5 | mM | 100 | | 1 |
| Horse radish peroxidase | 0.01 | U/ml | 10 | | 0.2 |
| dd H$_2$O | | | | | 88.52 |
| | | | | | 160.00 |
| Purified enzyme | | | | | 40.00 |
| Assay volume | | | | | 200.00 |

The enzymatic assay was used to define the enzyme activity.

2.2 Cytosolic Sheep Liver Aldehyde-Dehydrogenase (slA-lDH)

The gene slalDH for the cytosolic liver enzyme aldehyde-dehydrogenase from *Ovies aries* was a synthetic gene codon-optimized for expression in *Escherichia coli*. It was cloned into a derivative of pET28a with an alternative MCS carrying additionally the recognition sites for the two restriction-endonucleases BsaI and BfuAI.

The enzyme expression was done with an autoinduction-media developed by F. W. Studier and colleagues. The method is based upon a buffered medium that contains a mixture of carbon sources, including lactose. The medium allows the recombinant protein expression without any additional inducer substances. In the following section the reagents and stock solutions are described:

ZY
10 g tryptone
5 g yeast extract
925 ml water
20×NPS

| Component | 1 liter | mol/liter |
|---|---|---|
| dd H$_2$O | — | |
| (NH$_4$)$_2$SO$_4$ | 66 g | 0.5M |
| KH$_2$PO$_4$ | 136 g | 1M |
| Na$_2$HPO$_4$ | 142 g | 1M |

50×5052

| Component | 1 liter |
|---|---|
| Glycerol (weigh in beaker) | 250 g |
| H$_2$O | 730 ml |
| Glucose | 25 g |
| α-Lactose | 100 g |

1 M MgSO$_4$
24.65 g MgSO$_4$.7H$_2$O
Water to make 100 ml
ZYP-5052 Rich Medium for Auto-Induction
Add 1 M MgSO$_4$ before adding 20×NPS to avoid precipitate
Kanamycin is used at significantly higher concentrations (100 µg/ml) than is normally (25-40 Ng/ml). Studier has found that in the T7 expression strains in these rich media, it does not provide adequate selection at the lower concentration

| Component | 200 ml |
|---|---|
| ZY | 186 ml |
| 1M MgSO$_4$ | 0.2 ml |
| 50× 5052 | 4 ml |
| 20× NPS | 10 ml |
| Kanamycin (30 mg/ml) | 0.667 ml |

The plasmid pCBR-NH-slaldh-O.a. carrying the cytosolic liver aldehyde-dehydrogenase from *Ovies aries* was used to transform *E. coli* BL21 (DE3) for use for protein expression. The recombinant *E. coli* BL21 strain was cultivated in auto-induction media described above with the following procedure. First the bacteria culture was cultivated at 37° C. and 150 rpm for 3 h, after that the culture was transferred to 16° C. at 150 rpm for additionally 21 h.

Figure 8:
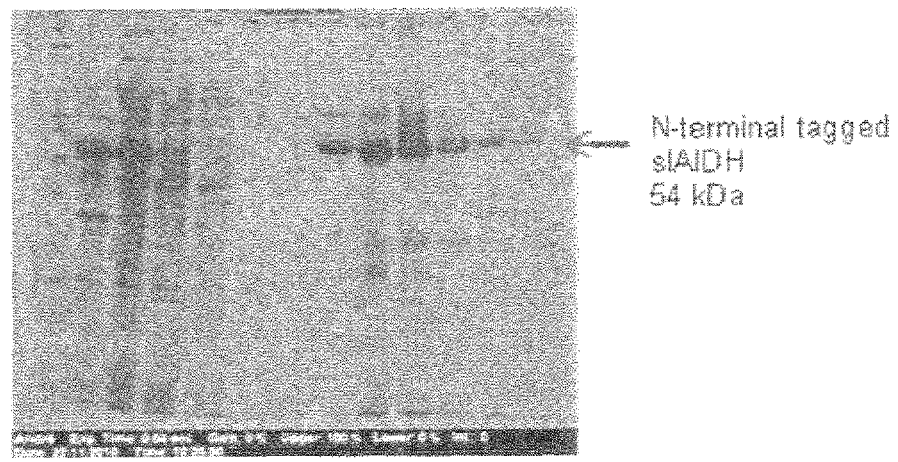
FIG. 8 shows the analysis of the product of the purification of aldehyde dehydrogenase from $Ovies$ $aries$.

After centrifugation, cells were frozen or directly used and suspended in Lysis/Wash Buffer (50 mM phosphate, pH 8.0, 500 mM NaCl, 10% glycerol, 20 mM imidazole) and for that 1 g of cells were resuspended in 10 ml Buffer. For cell disruption a cell-disrupter was used. After this step 10 µl DNase Stock-Solution (10 mg/ml DNase) per 10 ml and 25 µl of 1 M MgSO$_4$ were added and incubated for 20 min at room temperature for DNA cleavage. After centrifugation 45 min at 40.000 g at 4° C. to clarify the cell extract, the supernatant was loaded on a 5 ml HisTrap FF column (GE Health Care Europe) using a Äkta Purifier 100 (GE Health Care Europe). After sample loading, the column was washed with 5 volumes of Lysis/Wash Buffer and the protein was eluted with the same buffer containing 500 mM imidazole. In the final step the buffer exchange was done using a HiPrep26/10 desalting column (GE Health Care Europe) with a mobile phase composed of 50 mM TRIS, pH 8.0. After this the protein was tested in an activity assay and stored preparing glycerol stocks (1:1 dilution with 50% glycerol). The analysis of the product is shown in FIG. 8.

Enzyme activity on acetaldehyde as substrate of the purified enzyme was measured by monitoring initial NADH Generation at 340 nm at 25° C. The assay was done in 96-well microtiter plates containing the following components:

| Component | Assay conc. | Unit | Stock solution conc. | Unit | Stock solution pro well (µl) |
|---|---|---|---|---|---|
| TRIS (pH 8.0) | 25.00 | mM | 250.0 | mM | 20.00 |
| NAD$^+$ | 1.0 | mM | 20.0 | mM | 10.00 |
| D-Glucuronate | 20.00 | mM | 100.00 | mM | 40.00 |
| dd H$_2$O | | | | | 125.00 |
| | | | | | 195.00 |
| Purified enzyme | | | | | 5.00 |
| Assay volume | | | | | 200.00 |

Figure 9:
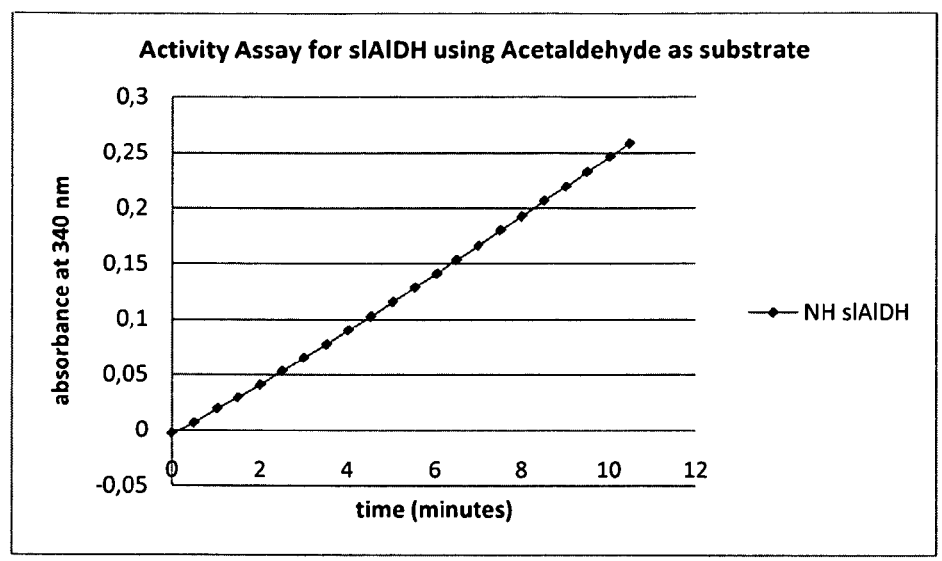
FIG. 9 shows the results of the activity assay for slAlDH using acetaldehyde as substrate.

The enzymatic assay was used to define the enzyme activity. The results are shown in FIG. 9.

2.3 Uronate-Dehydrogenase from *Agrobacterium tumefaciens* C58 (Udh)

The gene udh for the enzyme uronate-dehydrogenase from *Agrobacterium tumefaciens* C58 was a synthetic gene codon-optimized for expression in *Escherichia coli*. It was cloned into a derivative of pET28a with an alternative MCS carrying additionally the recognition sites for the two restriction-endonucleases BsaI and BfuAI.

The enzyme expression was done with an autoinduction-media developed by F. W. Studier and colleagues. The method is based upon a buffered medium that contains a mixture of carbon sources, including lactose. The medium allows the recombinant protein expression without any additional inducer substances. In the following section the reagents and stock solutions are described:

ZY
10 g tryptone
5 g yeast extract
925 ml water
20×NPS

| Component | 1 liter | mol/liter |
|---|---|---|
| dd H$_2$O | — | |
| (NH$_4$)$_2$SO$_4$ | 66 g | 0.5M |
| KH$_2$PO$_4$ | 136 g | 1M |
| Na$_2$HPO$_4$ | 142 g | 1M |

50×5052

| Component | 1 liter |
|---|---|
| Glycerol (weigh in beaker) | 250 g |
| H$_2$O | 730 ml |
| Glucose | 25 g |
| α-Lactose | 100 g |

1 M MgSO$_4$
24.65 g MgSO$_4$.7H$_2$O
Water to make 100 ml
ZYP-5052 rich medium for auto-induction
Add 1 M MgSO$_4$ before adding 20×NPS to avoid precipitate
Kanamycin is used at significantly higher concentrations (100 µg/ml) than is normally (25-40 µg/ml). Studier has found that in the T7 expression strains in these rich media, it does not provide adequate selection at the lower concentration

| Component | 200 ml |
|---|---|
| ZY | 186 ml |
| 1M MgSO$_4$ | 0.2 ml |
| 50x 5052 | 4 ml |
| 20x NPS | 10 ml |
| Kanamycin (30 mg/ml) | 0.667 ml |

The plasmid pCBR-NH-udh-A.t. carrying the uronate-dehydrogenase from *Agrobacterium tumefaciens* C58 was used to transform *E. coli* BL21 (DE3) for use for protein expression. The recombinant *E. coli* BL21 strain was cultivated in auto-induction media described above with the following procedure. First the bacteria culture was cultivated at 37° C. and 150 rpm for 3 h, after that the culture was transferred to 16° C. at 150 rpm for additionally 21 h.

Figure 10:
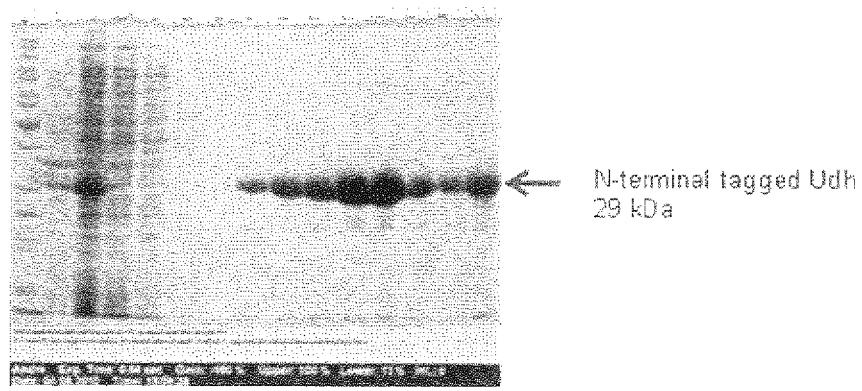
FIG. 10 shows the analysis of the product of the purification of uronate dehydrogenase from $Agrobacterium$ $tumefaciens$ C58.

After centrifugation, cells were frozen or directly used and suspended in Lysis/Wash Buffer (50 mM phosphate, pH 8.0, 500 mM NaCl, 10% glycerol, 20 mM imidazole) and for that 1 g of cells were resuspended in 10 ml Buffer. For cell disruption a cell-disrupter was used. After this step 10 µl DNase Stock-Solution (10 mg/ml DNase) per 10 ml and 25 µl of 1 M MgSO$_4$ were added and incubated for 20 min at room temperature for DNA cleavage. After centrifugation 45 min at 40.000 g at 4° C. to clarify the cell extract, the supernatant was loaded on a 5 ml HisTrap FF column (GE Health Care Europe) using a Äkta Purifier 100 (GE Health Care Europe). After sample loading, the column was washed with 5 volumes of Lysis/Wash Buffer and the protein was eluted with the same buffer containing 500 mM imidazole. In the final step the buffer exchange was done using a HiPrep26/10 desalting column (GE Health Care Europe) with a mobile phase composed of 50 mM TRIS, pH 8.0. The analysis of the product is shown in FIG. 10.

After this the protein was tested in an activity assay and stored preparing glycerol stocks (1:1 dilution with 50% glycerol).

Enzyme activity on glucuronate as substrate of the purified enzyme was measured by monitoring initial NADH Generation at 340 nm at 25° C. The assay was done in 96-well microtiter plates containing the following components:

| Component | Assay conc. | Unit | Stock solution conc. | Unit | Stock solution pro well (µl) |
|---|---|---|---|---|---|
| TRIS (pH 8.0) | 100.00 | mM | 250.0 | mM | 80.00 |
| NAD$^+$ | 1.0 | mM | 20.0 | mM | 10.00 |
| D-Glucuronate | 10.00 | mM | 100.00 | mM | 20.00 |
| dd H$_2$O | | | | | 85.00 |
| | | | | | 195.00 |
| Purified enzyme | | | | | 5.00 |
| Assay volume | | | | | 200.00 |

Figure 11:
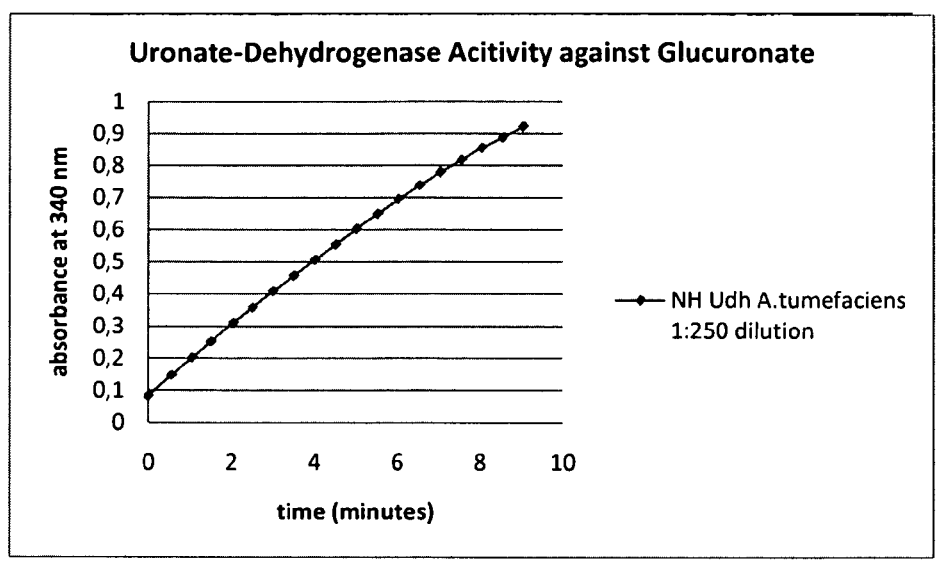
FIG. 11 shows the results of the activity assay for uronate dehydrogenase using glucuronate as substrate.

The enzymatic assay was used to define the enzyme activity. The results are shown in FIG. 11. The enzyme activity was 318 U/ml.

2.4 Glucarate-Dehydratase from *Actinobacillus succinogenes* 130 Z (GlucD)

The gene glucD for the enzyme glucarate-dehydratase from *Actinobacillus succinogenes* 130 Z was a synthetic gene codon-optimized for expression in *Escherichia coli*. It was cloned into a derivative of pET28a with an alternative MCS carrying additionally the recognition sites for the two restriction-endonucleases BsaI and BfuAI.

The enzyme expression was done with a modified terrific broth medium containing additionally 1 M sorbitol and 5 mM betaine.

Terrific-Broth

| Component | 1 liter |
|---|---|
| Casein | 12 g |
| Yeast extract | 24 g |
| Sorbitol | 182 g |
| $K_2HPO_4$ | 12.5 g |
| $KH_2PO_4$ | 2.3 g |

5 M Betaine Stock Solution 58.575 g ad. 100 ml $H_2O$

The plasmid pCBR-NH-glucD-A.s. carrying the glucarate-dehydratase from *Actinobacillus succinogenes* 130 Z was used to transform *E. coli* BL21 (DE3) for use for protein expression. The recombinant *E. coli* BL21 strain was cultivated in terrific broth medium containing 1 M sorbitol, 5 mM betaine and 90 µg/ml kanamycin. The bacteria culture was cultivated at 37° C. at 150 rpm until reaching an $A_{600}$ of 1. Isopropyl β-D-thiogalactopyranoside was added at a concentration of 250 µM to induce protein production, and the culture was transferred to 16° C. at 150 rpm for additionally 16 h.

Figure 12:
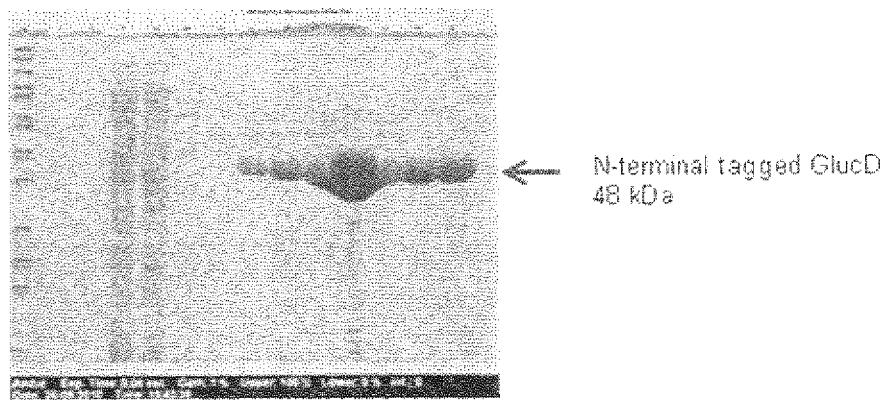
FIG. 12 shows the analysis of the product of the purification of glucarate dehydratase from $Actinobacillus$ $succinogenes$ 130 Z.

After centrifugation, cells were frozen or directly used and suspended in Lysis/Wash Buffer (50 mM phosphate, pH 8.0, 500 mM NaCl, 10% glycerol, 20 mM imidazole) and for that 1 g of cells were resuspended in 10 ml Buffer. For cell disruption a cell-disrupter was used. After this step 10 µl DNase Stock-Solution (10 mg/ml DNase) per 10 ml and 25 µl of 1 M $MgSO_4$ were added and incubated for 20 min at room temperature for DNA cleavage. After centrifugation 45 min at 40.000 g at 4° C. to clarify the cell extract, the supernatant was loaded on a 5 ml HisTrap FF column (GE Health Care Europe) using a Äkta Purifier 100 (GE Health Care Europe). After sample loading, the column was washed with 5 volumes of Lysis/Wash Buffer and the protein was eluted with the same buffer containing 500 mM imidazole. In the final step the buffer exchange was done using a HiPrep26/10 desalting column (GE Health Care Europe) with a mobile phase composed of 50 mM TRIS, pH 8.0, 50 mM NaCl, 10% glycerol and 1 mM dithiothreitol. The analysis of the product is shown in FIG. 12.

After this, the protein was tested in an activity assay and stored preparing glycerol stocks (1:1 dilution with 50% glycerol).

Enzyme activity on glucarate as substrate of the purified enzyme was measured by semicarbazide assay at 250 nm at 25° C. The assay was done in 96-well UV-microtiter plates containing the following components:

| Component | Assay conc. | Unit | Stock solution conc. | Unit | Stock solution pro well (µl) |
|---|---|---|---|---|---|
| HEPES (pH 7.5), 100 mM NaCl, 10% Glycerol | 43.50 | mM | 50.0 | mM | 174.00 |
| $MgCl_2$ | 5.0 | mM | 1000.0 | mM | 1.00 |
| Glucarate | 10.00 | mM | 100.00 | mM | 20.00 |
| Purified enzyme | | | | | 195.00 5.00 |
| Assay volume | | | | | 200.00 |

Figure 13:
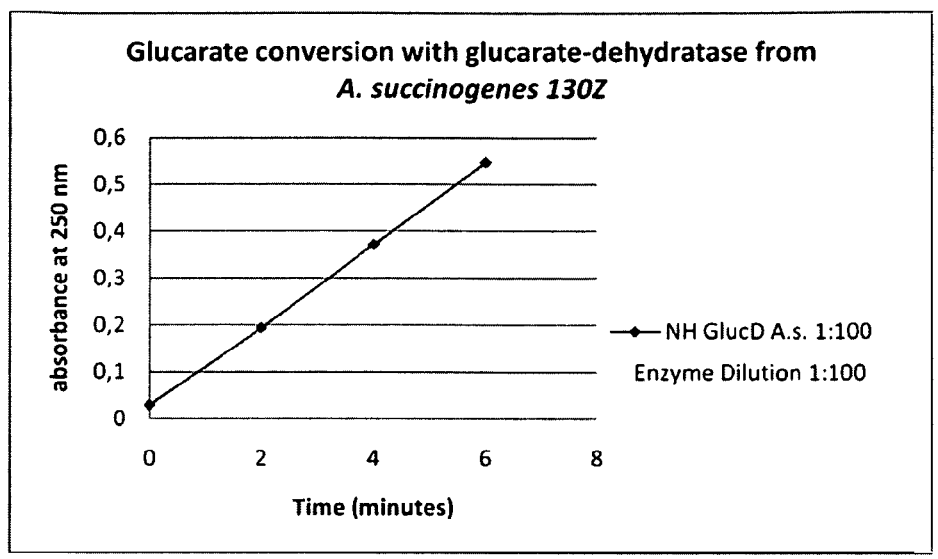
FIG. 13 shows the results of the activity assay for glucarate dehydratase using glucarate as substrate.

The enzymatic assay was used to define the enzyme activity. The results are shown in FIG. 13. The enzyme activity was 289 U/ml.

2.5 Keto-deoxy-Glucarate-Dehydratase from *Acinetobacter baylyi* ADP 1 (KdgD)

The gene kdgD for the enzyme keto-deoxy-glucarate-dehydratase from *Acinetobacter baylyi* ADP1 was a synthetic gene codon-optimized for expression in *Escherichia coli*. It was cloned into a derivative of pET28a with an alternative MCS carrying additionally the recognition sites for the two restriction-endonucleases BsaI and BfuAI.

The enzyme expression was done with a modified terrific broth medium containing additionally 1M sorbitol and 5 mM betaine.

Terrific-Broth

| Component | 1 liter |
|---|---|
| Casein | 12 g |
| Yeast extract | 24 g |
| Sorbitol | 182 g |
| $K_2HPO_4$ | 12.5 g |
| $KH_2PO_4$ | 2.3 g |

5 M Betaine Stock solution 58.575 g ad. 100 ml $H_2O$

The plasmid pCBR-NH-KdgD-A.b. carrying the keto-deoxy-glucarate-dehydratase from *Acinetobacter baylyi* ADP1 was used to transform *E. coli* BL21 (DE3) for use for protein expression. The recombinant *E. coli* BL21 strain was cultivated in terrific broth medium containing 1 M sorbitol, 5 mM betaine and 90 µg/ml kanamycin. The bacteria culture was cultivated at 37° C. at 150 rpm until reaching an $A_{600}$ of 1. Isopropyl β-D-thiogalactopyranoside was added at a concentration of 250 µM to induce protein production, and the culture was transferred to 16° C. at 150 rpm for additionally 16 h.

Figure 14:
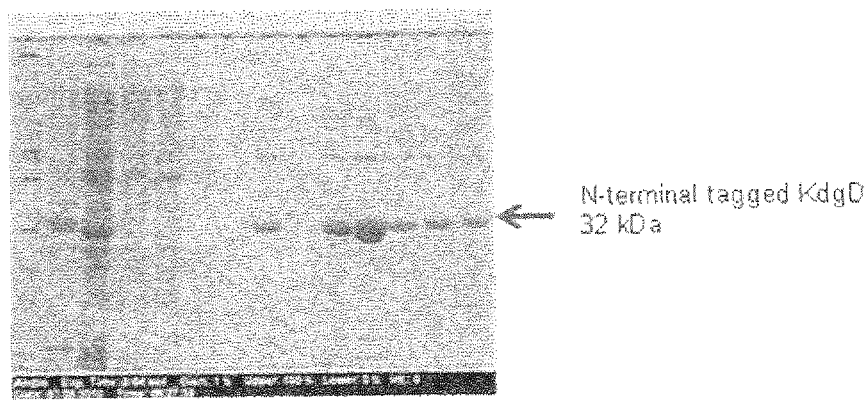
FIG. 14 shows the analysis of the product of the purification of Keto-deoxy-Glucarate-Dehydratase from $Acinetobacter$ $baylyi$ ADP1.

After centrifugation, cells were frozen or directly used and suspended in Lysis/Wash Buffer (50 mM phosphate, pH 8.0, 500 mM NaCl, 10% glycerol, 20 mM imidazole) and for that 1 g of cells were resuspended in 10 ml Buffer. For cell disruption a cell-disrupter was used. After this step 10 µl DNase Stock-Solution (10 mg/ml DNase) per 10 ml and 25 µl of 1 M $MgSO_4$ were added and incubated for 20 min at room temperature for DNA cleavage. After centrifugation 45 min at 40.000 g at 4° C. to clarify the cell extract, the supernatant was loaded on a 5 ml HisTrap FF column (GE Health Care Europe) using a Äkta Purifier 100 (GE Health Care Europe). After sample loading, the column was washed with 5 volumes of Lysis/Wash Buffer and the protein was eluted with the same buffer containing 500 mM imidazole. In the final step the buffer exchange was done using a HiPrep26/10 desalting column (GE Health Care Europe) with a mobile phase composed of 50 mM TRIS, pH 8.0, 50 mM NaCl, 10% glycerol and 1 mM dithiothreitol. After this the protein was tested in an activity assay and stored preparing glycerol stocks (1:1 dilution with 50% glycerol). The analysis of the product is shown in FIG. 14.

Enzyme activity on keto-deoxy-glucarate as substrate of the purified enzyme was measured by coupled assay using an aldehyde dehydrogenase to generate α-keto-glutarate at 340 nm at 25° C. The assay was done in 96-well microtiter plates containing the following components:

| Component | Assay conc. | Unit | Stock solution conc. | Unit | Stock solution pro well (µl) |
|---|---|---|---|---|---|
| HEPES (pH 7.5), 100 mM NaCl, 10% Glycerol | 32.12 | mM | 50.0 | mM | 129.25 |
| MgCl$_2$ | 3.75 | mM | 1000.0 | mM | 0.75 |
| NAD$^+$ | 1.0 | mM | 20.00 | mM | 10.00 |
| Keto-deoxy-Glucarate | 10.00 | mM | 40.00 | mM | 50.00 |
| Aldehyde dehydrogenase | | | | | 5.0 |
| | | | | | 195.00 |
| Purified enzyme | | | | | 5.00 |
| Assay volume | | | | | 200.00 |

Figure 15:
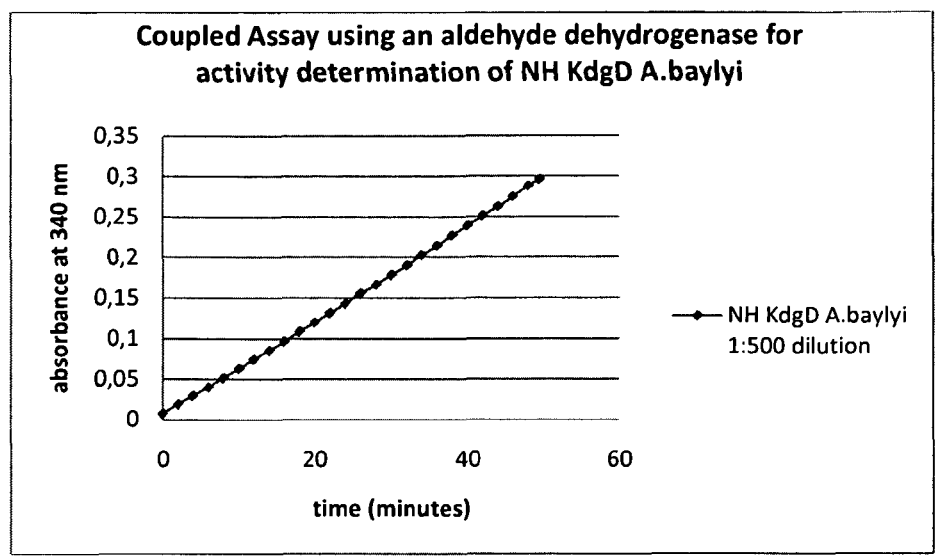
FIG. 15 shows the results of the activity assay for Keto-deoxy-Glucarate-Dehydratase using keto-deoxy-glucarate as substrate.

The enzymatic assay was used to define the enzyme activity. The results are shown in FIG. 15. The enzyme activity was 32 U/ml.

2.6 Alcohol-Dehydrogenase from *Escherichia coli* K-12 (YjgB)

The gene yjgB for the enzyme alcohol-dehydrogenase from *Escherichia coli* K-12 was cloned from genomic DNA for expression in *Escherichia coli*. It was cloned into a pET28a using the two restriction endonucleases NcoI and XhoI.

The enzyme expression was done with an autoinduction-media developed by F. W. Studier and colleagues. The method is based upon a buffered medium that contains a mixture of carbon sources, including lactose. The medium allows the recombinant protein expression without any additional inducer substances. In the following section the reagents and stock solutions are described:

ZY
10 g tryptone
5 g yeast extract
925 ml water
20×NPS

| Component | 1 liter | mol/liter |
|---|---|---|
| dd H$_2$O | — | |
| (NH$_4$)$_2$SO$_4$ | 66 g | 0.5M |
| KH$_2$PO$_4$ | 136 g | 1M |
| Na$_2$HPO$_4$ | 142 g | 1M |

50×5052

| Component | 1 liter |
|---|---|
| Glycerol (weigh in beaker) | 250 g |
| H$_2$O | 730 ml |

| Component | 1 liter |
|---|---|
| Glucose | 25 g |
| α-Lactose | 100 g |

1 M MgSO$_4$
24.65 g MgSO$_4$.7H$_2$O
Water to make 100 ml
100 mM ZnSO$_4$
0.287 g ZnSO$_4$.7H$_2$O
Water to make 10 ml
ZYP-5052 Rich Medium for Auto-Induction
Add 1 M MgSO$_4$ before adding 20×NPS to avoid precipitate
Kanamycin is used at significantly higher concentrations (100 µg/ml) than is normally (25-40 µg/ml). Studier has found that in the T7 expression strains in these rich media, it does not provide adequate selection at the lower concentration

| Component | 200 ml |
|---|---|
| ZY | 186 ml |
| 1M MgSO$_4$ | 0.2 ml |
| 50x 5052 | 4 ml |
| 20x NPS | 10 ml |
| 100 mM ZnSO$_4$ | 0.2 ml |
| Kanamycin (30 mg/ml) | 0.667 ml |

The plasmid pET28a-NH-yjgB-E.c. carrying the alcohol-dehydrogenase from *Escherichia coli* was used to transform *E. coli* BL21 (DE3) for use for protein expression. The recombinant *E. coli* BL21 strain was cultivated in auto-induction media described above with the following procedure. First the bacteria culture was cultivated at 37° C. and 150 rpm for 3 h, after that the culture was transferred to 16° C. at 150 rpm for additionally 21 h.

Figure 16:
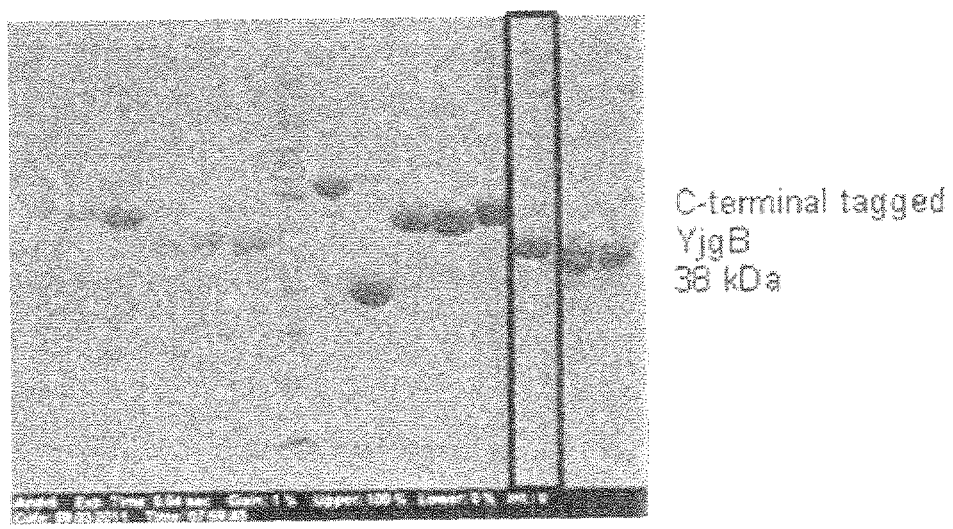
FIG. 16 shows the analysis of the product of the purification of alcohol-dehydrogenase from $Escherichia$ $coli$ K-12 (YjgB).

After centrifugation, cells were frozen or directly used and suspended in Lysis/Wash Buffer (50 mM phosphate, pH 8.0, 500 mM NaCl, 10% glycerol, 20 mM imidazole) and for that 1 g of cells were resuspended in 10 ml Buffer. For cell disruption a cell-disrupter was used. After this step 10 µl DNase Stock-Solution (10 mg/ml DNase) per 10 ml and 25 µl of 1 M MgSO$_4$ were added and incubated for 20 min at room temperature for DNA cleavage. After centrifugation 45 min at 40.000 g at 4° C. to clarify the cell extract, the supernatant was loaded on a 5 ml HisTrap FF column (GE Health Care Europe) using a Äkta Purifier 100 (GE Health Care Europe). After sample loading, the column was washed with 5 volumes of Lysis/Wash Buffer and the protein was eluted with the same buffer containing 500 mM imidazole. In the final step the buffer exchange was done using a HiPrep26/10 desalting column (GE Health Care Europe) with a mobile phase composed of 50 mM TRIS, pH 8.0. After this the protein was tested in an activity assay and stored at −20° C. The analysis of the product is shown in FIG. 16.

Enzyme activity on 2,5-dioxo-pentanoate as substrate of the purified enzyme was measured with a coupled assay using keto-deoxy-glucarate-dehydratase to produce the substrate for YjgB from keto-deoxy-glucarate at 340 nm at 25° C. The assay was done in 96-well microtiter plates containing the following components:

| Component | Assay conc. | Unit | Stock solution conc. | Unit | Stock solution pro well (µl) |
|---|---|---|---|---|---|
| HEPES (pH 7.5), 100 mM NaCl, 10% Glycerol | 31.06 | mM | 50.0 | mM | 124.25 |
| MgCl$_2$ | 3.75 | mM | 1000.0 | mM | 0.75 |
| NADPH | 0.3 | mM | 4.00 | mM | 15.00 |
| Keto-deoxy-Glucarate | 10.00 | mM | 40.00 | mM | 50.00 |
| Keto-deoxy-Glucarate dehydratase | | | | | 5.0 |
| | | | | | 195.00 |
| Purified enzyme | | | | | 5.00 |
| Assay volume | | | | | 200.00 |

Figure 17:
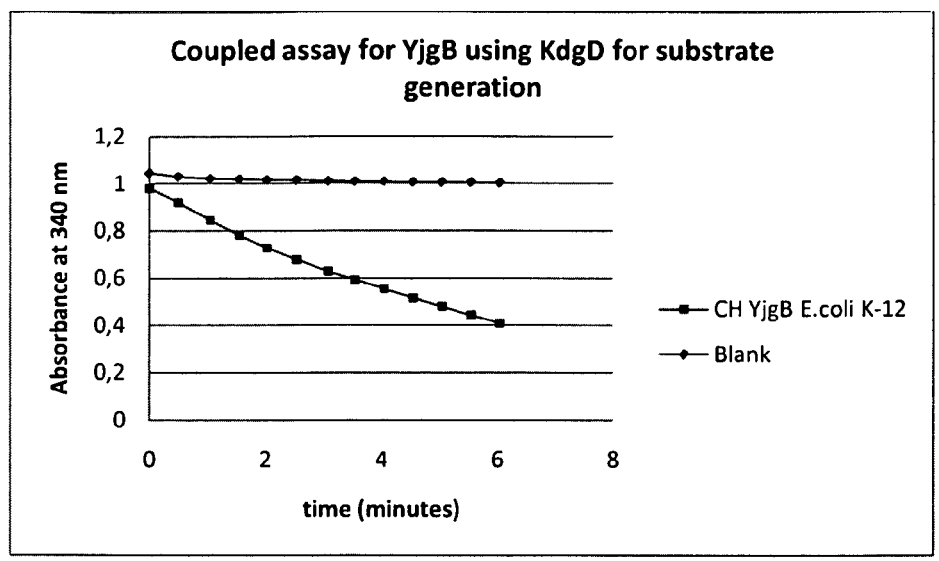
FIG. 17 shows the results of the activity assay for alcohol-dehydrogenase from $Escherichia$ $coli$ K-12 (YjgB) using 2,5-dioxo-pentanoate as substrate.

The enzymatic assay was used to define the enzyme activity. The results are shown in FIG. 17. The enzyme activity was 1.7 U/ml.

2.7 KdcA from *Lactococcus lactis* IL1403

For the decarboxylation of 5-hydroxy-2-oxo-pentanoate a branched-chain decarboxylase from *Lactococcus lactis* IL1403 can be used. The enzyme was prepared as described in Adv. Synth. Catal. 2007, 349, 1425-1435.

2.8 Alcohol-dehydrogenase from *Escherichia coli* K-12 (YqhD)

The gene yqhD for the enzyme alcohol-dehydrogenase from *Escherichia coli* K-12 was cloned from genomic DNA for expression in *Escherichia coli*. It was cloned into a pET28a using the two restriction endonucleases NcoI and XhoI.

The enzyme expression was done with a modified terrific broth medium containing additionally 1 M sorbitol and 5 mM betaine.

Terrific-Broth

| Component | 1 liter |
|---|---|
| Casein | 12 g |
| Yeast extract | 24 g |
| Sorbitol | 182 g |
| K$_2$HPO$_4$ | 12.5 g |
| KH$_2$PO$_4$ | 2.3 g |

5 M Betaine Stock Solution
58.575 g
Water to make 100 ml H$_2$O
100 mM ZnSO$_4$
0.287 g ZnSO$_4$.7H$_2$O
Water to make 10 ml The plasmid pET28a-CH-yjgB-E.c. carrying the alcohol-dehydrogenase from *Escherichia coli* K-12 was used to transform *E. coli* BL21 (DE3) for use for protein expression. The recombinant *E. coli* BL21 strain was cultivated in terrific broth medium containing 1 M sorbitol, 5 mM betaine, 0.1 mM ZnSO$_4$ and 90 µg/ml kanamycin. The bacteria culture was cultivated at 37° C. at 150 rpm until reaching an A$_{600}$ of 1. Isopropyl β-D-thiogalactopyranoside was added at a concentration of 250 µM to induce protein production, and the culture was transferred to 16° C. at 150 rpm for additionally 16 h.

Figure 18:
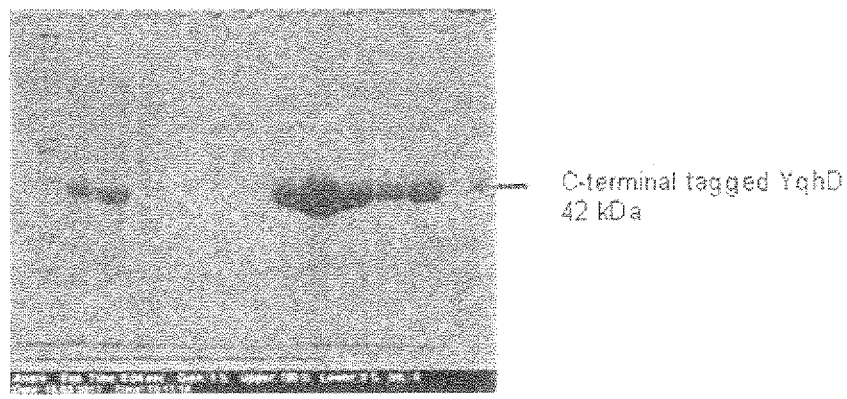
FIG. 18 shows the analysis of the product of the purification of alcohol dehydrogenase from $Escherichia$ $coli$ K-12.

After centrifugation, cells were frozen or directly used and suspended in Lysis/Wash Buffer (50 mM phosphate, pH 8.0, 500 mM NaCl, 10% glycerol, 20 mM imidazole) and for that 1 g of cells were resuspended in 10 ml Buffer. For cell disruption a cell-disrupter was used. After this step 10 µl DNase Stock-Solution (10 mg/ml DNase) per 10 ml and 25 µl of 1 M MgSO$_4$ were added and incubated for 20 min at room temperature for DNA cleavage. After centrifugation 45 min at 40.000 g at 4° C. to clarify the cell extract, the supernatant was loaded on a 5 ml HisTrap FF column (GE Health Care Europe) using a Äkta Purifier 100 (GE Health Care Europe). After sample loading, the column was washed with 5 volumes of Lysis/Wash Buffer and the protein was eluted with the same buffer containing 500 mM imidazole. In the final step the buffer exchange was done using a HiPrep26/10 desalting column (GE Health Care Europe) with a mobile phase composed of 50 mM TRIS, pH 8.0. After this the protein was tested in an activity assay and stored preparing glycerol stocks (1:1 dilution with 50% glycerol). The analysis of the product is shown in FIG. 18.

Example 3

Analysis of Intermediates

Figure 19:
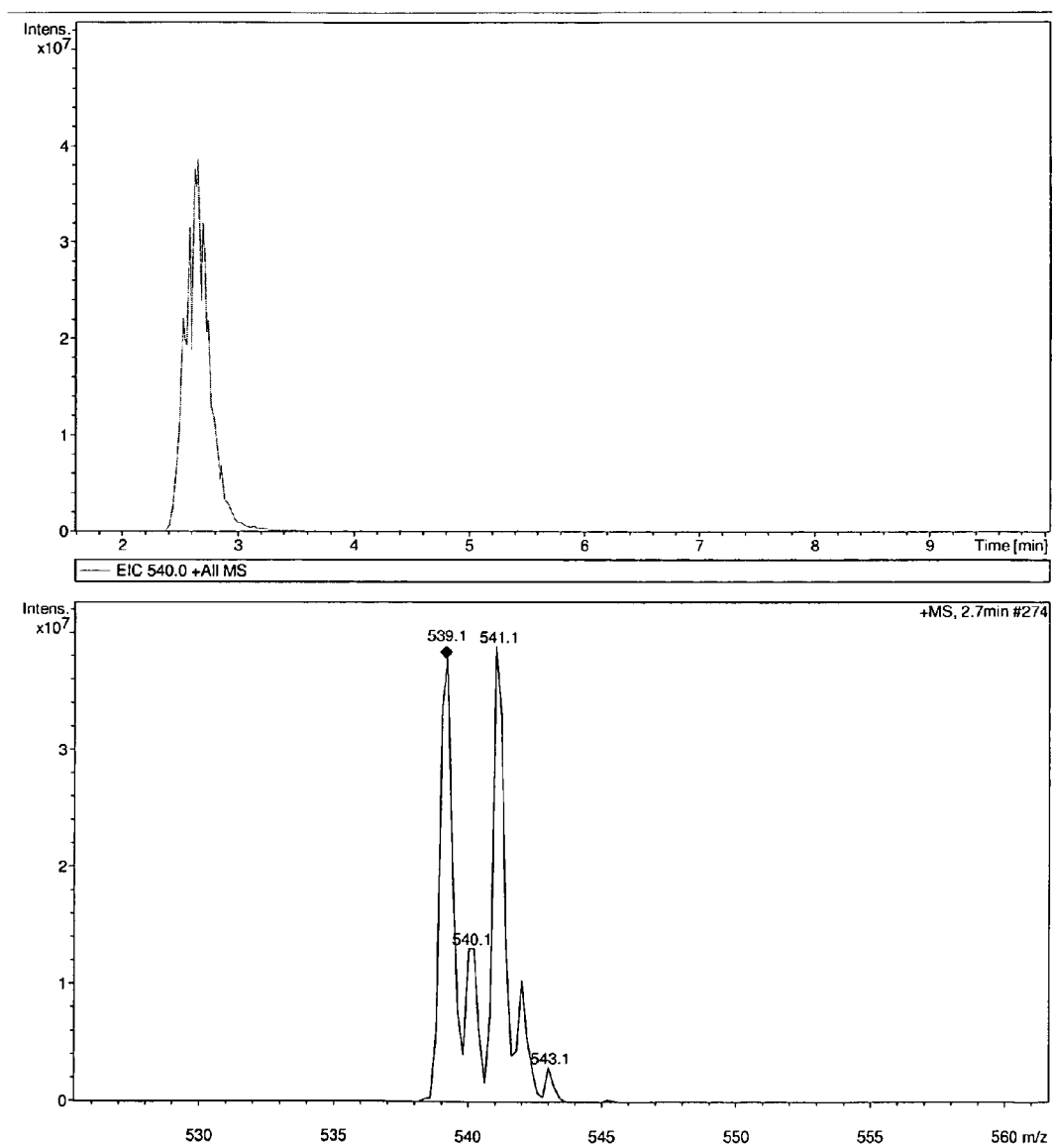
FIG. 19 shows the analysis of intermediates using HPLC-MS (Example 3): D-glucuronic derivative, upper panel: elution time, lower panel: mass values detected
Figure 20:
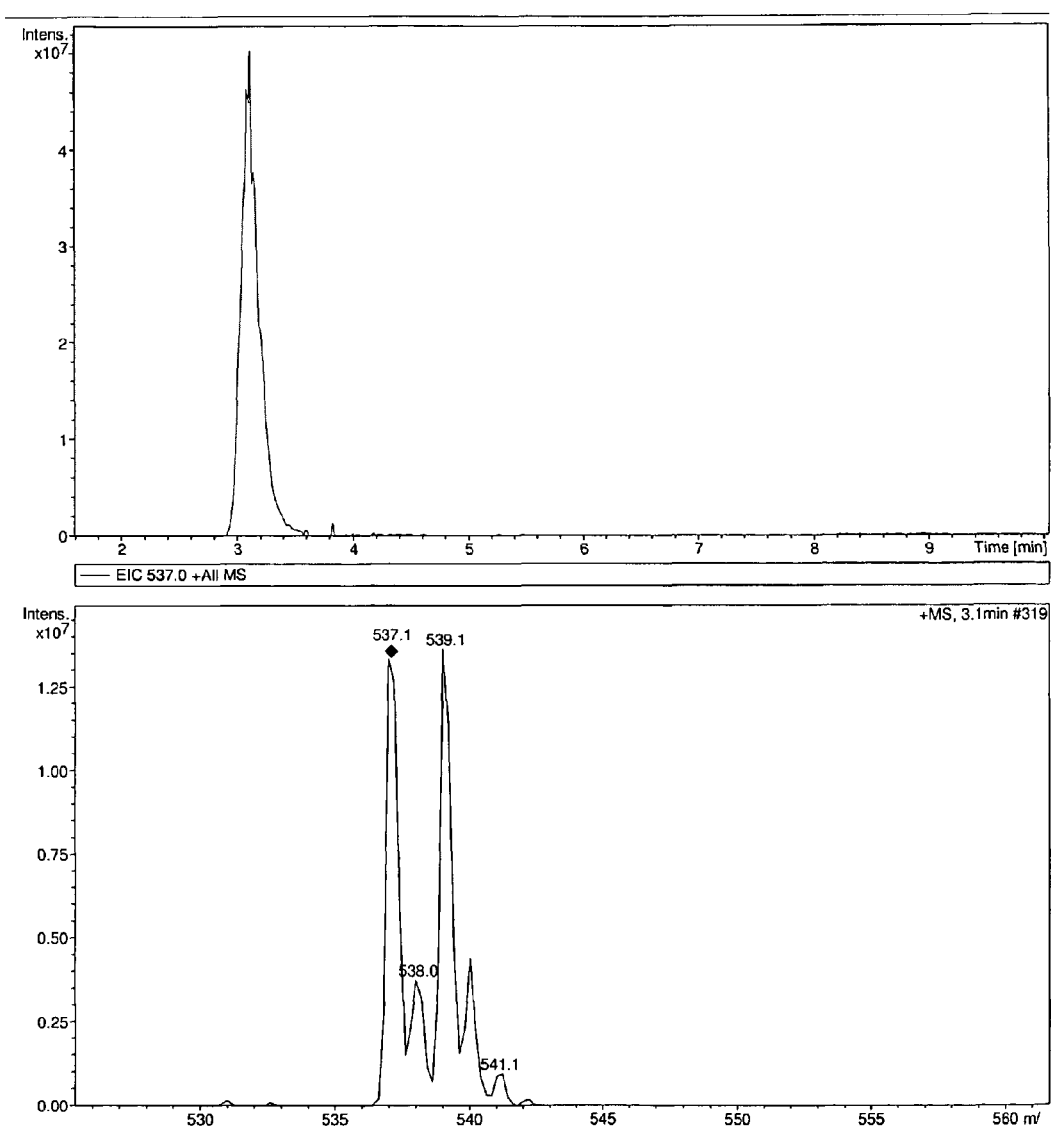
FIG. 20 shows the analysis of intermediates using HPLC-MS (Example 3): D-glucaric acid derivative, upper panel: elution time, lower panel: mass values detected
Figure 21:
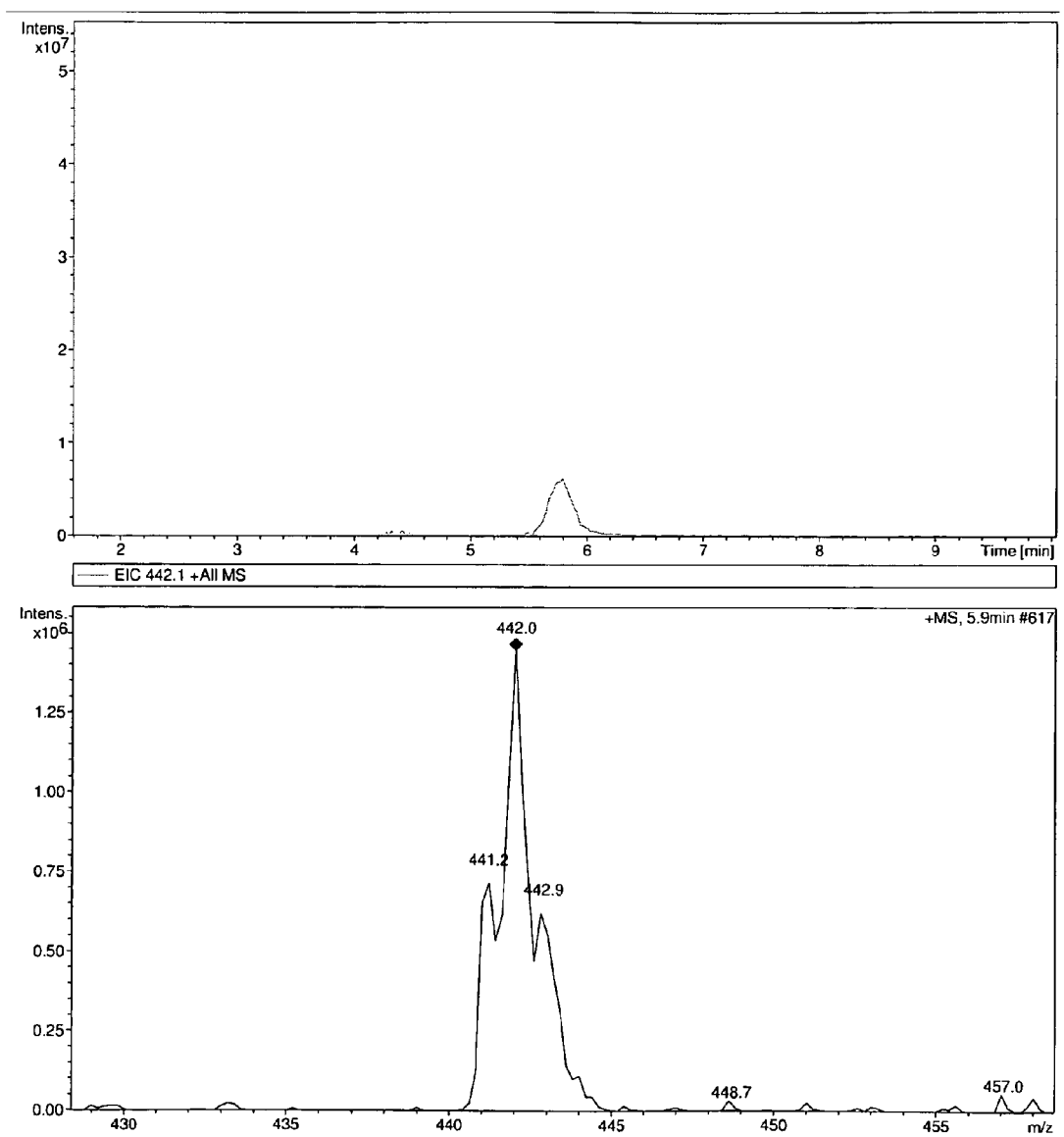
FIG. 21 shows the analysis of intermediates using HPLC-MS (Example 3): 5-keto-4-deoxy-glucuronic acid derivative, upper panel: elution time, lower panel: mass values detected (m/z=2)
Figure 22:
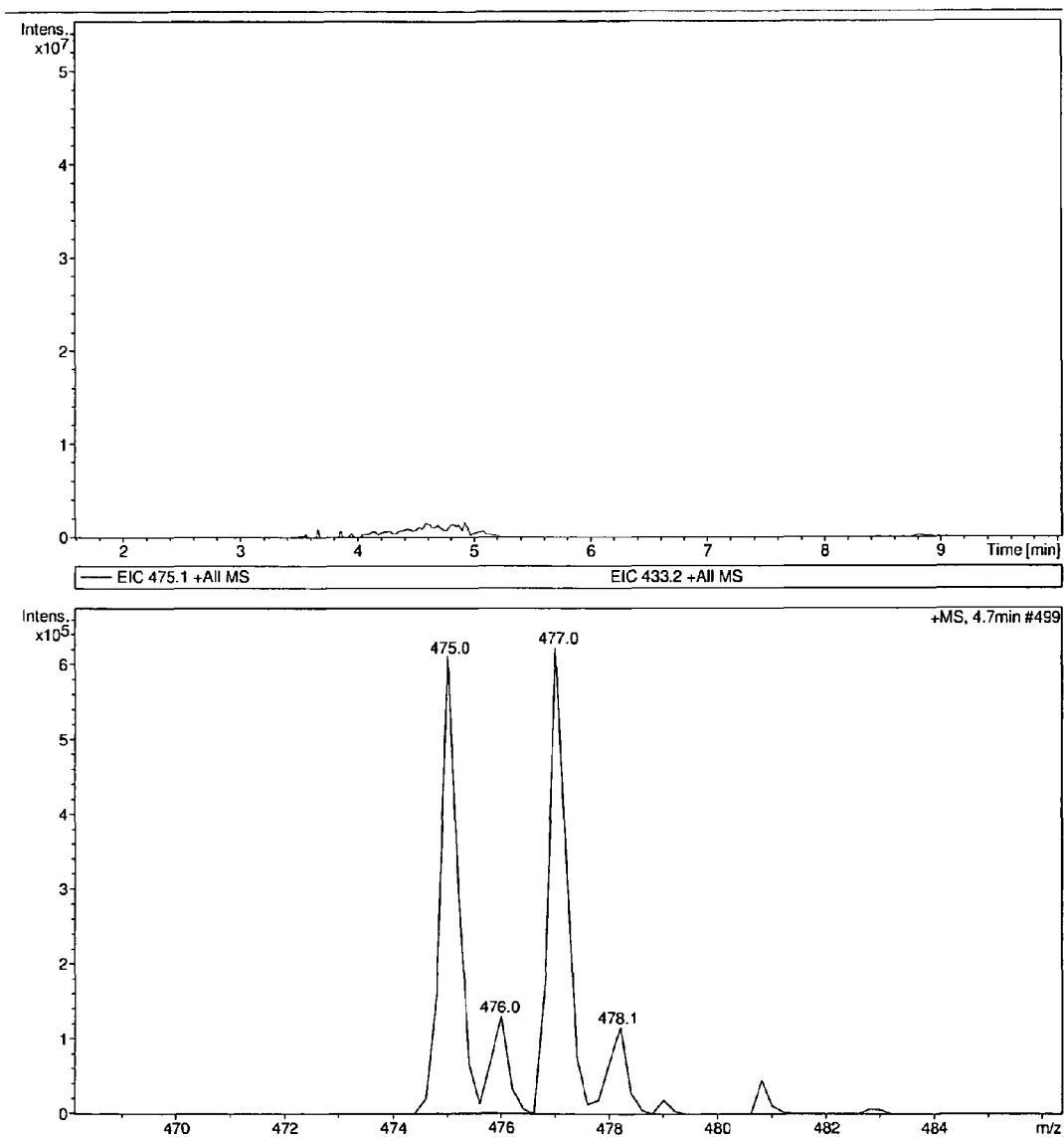
FIG. 22 shows the analysis of intermediates using HPLC-MS (Example 3): 2,5-dioxo-pentanoic acid derivative, upper panel: elution time, lower panel: mass values detected
Figure 23:
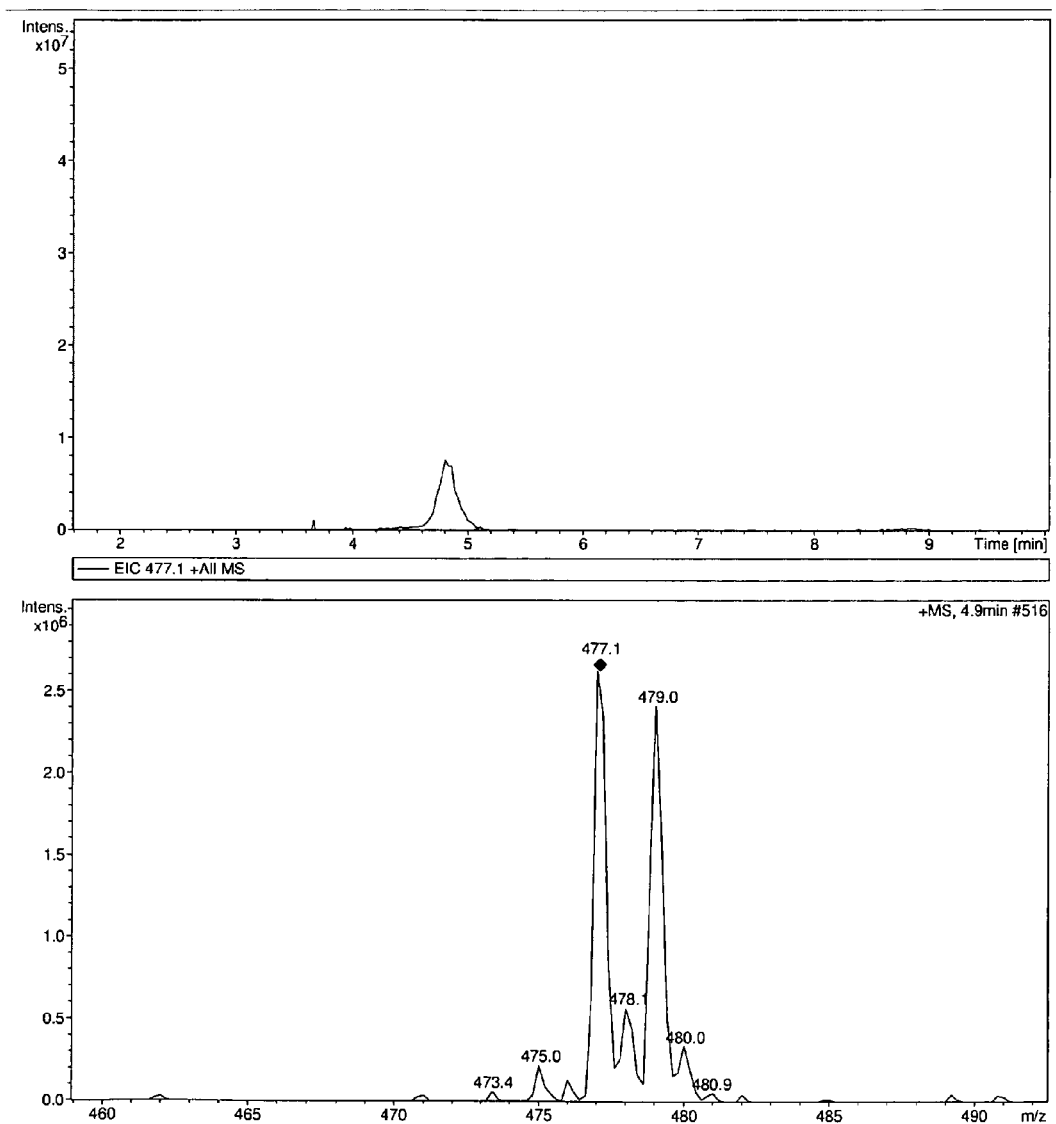
FIG. 23 shows the analysis of intermediates using HPLC-MS (Example 3): 5-hydroxy-2-oxo-pentanoic acid derivative, upper panel: elution time, lower panel: mass values detected

To identify different intermediates of the reaction described in Example 1 those carrying a carboxylic acid group were analysed by HPLC-MS. 150 µl of the sample of Example 1 were mixed with 200 µL of 8 mM 4-APEBA and 150 µL 125 mM EDC and incubated for 1 h at 20° C. [12]. Chromatographic separation was done with 0.1% formic acid as eluent and a gradient of acetonitrile. A Triart column (100×2 mm, 2 µm) was used. Detection was done by mass spectrometry. The appearance of specific mass values was monitored. The analysis showed the presence of glucuronic acid (FIG. 19), glucaric acid (FIG. 20), 5-keto-4-deoxy-glucaric acid (FIG. 21), 2,5-dioxopentanoic acid (FIG. 22) and 5-hydroxy-2-oxo-pentanoic acid (FIG. 23) supporting the invented pathway.

REFERENCES

1. Farrell, A. E., et al., *Ethanol Can Contribute to Energy and Environmental Goals*. Science, 2006. 311(5760): p. 506-508.
2. Morris, D., *The next economy: from dead carbon to living carbon*. Journal of the Science of Food and Agriculture, 2006. 86(12): p. 1743-1746.
3. Hempel, M., *Novel Process Windows—A Contribution to More Sustainable Chemistry?* Chemical Engineering & Technology, 2009. 32(11): p. 1651-1654.
4. Bechthold, I., et al., *Succinic Acid: A New Platform Chemical for Biobased Polymers from Renewable Resources*. Chemical Engineering & Technology, 2008. 31(5): p. 647-654.
5. Anastas, P. T. and J. B. Zimmerman, *Peer Reviewed: Design Through the 12 Principles of Green Engineering*. Environmental Science & Technology, 2003. 37(5): p. 94A-101A.
6. Werpy, T. and G. Petersen, *Top Value Added Chemicals from Biomass: Volume 1—Results of Screening for Potential Candidates from Sugars and Synthesis Gas*, in *Other Information: PBD: 1 August 2004*. 2004. p. Medium: ED; Size: 76 pp. pages.
7. Patel, M., et al., *Medium and Long-Term Opportunities and Risks of the Biotechnological Production of Bulk Chemicals from Renewable Resources—The Potential of White Biotechnology: The Brew Project, European Commission's GROWTH Programme (DG Reserach)*. 2006: Utrecht.

8. Haas, T., et al., *New diol processes: 1,3-propanediol and 1,4-butanediol.* Applied Catalysis A: General, 2005. 280 (1): p. 83-88.
9. Schmid, A., et al., *Industrial biocatalysis today and tomorrow.* Nature, 2001. 409(6817): p. 258-68.
10. Schoemaker, H. E., D. Mink, and M. G. Wubbolts, *Dispelling the Myths—Biocatalysis in Industrial Synthesis.* Science, 2003. 299(5613): p. 1694-1697.
11. Boysen, Mike M. K., *Carbohydrates as Synthetic Tools in Organic Chemistry.* Chemistry—A European Journal, 2007. 13(31): p. 8648-8659.
12. Eggink, M., et al., *Targeted LC-MS derivatization for aldehydes and carboxylic acids with a new derivatization agent 4-APEBA.* Analytical and Bioanalytical Chemistry, 2010, 397: 665-675

| SEQUENCES |
|---|
| Uronate-Dehydrogenase from *Agrobacterium tumefaciens* C 58 (SEQ ID NO: 1) |
| MKRLLVTGAA GQLGRVMRER LAPMAEILRL ADLSPLDPAG PNEECVQCDL ADANAVNAMV |
| AGCDGIVHLG GISVEKPFEQ ILQGNIIGLY NLYEAARAHG QPRIVFASSN HTIGYYPQTE |
| RLGPDVPARP DGLYGVSKCF GENLARMYFD KFGQETALVR IGSCTPEPNN YRMLSTWFSH |
| DDFVSLIEAV FRAPVLGCPV VWGASANDAG WWDNSHLGFL GWKPKDNAEA FRRHITETTP |
| PPDPNDALVR FQGGTFVDNP IFKQS |
| Glucarate-Dehydratase from *Actinobacillus succinogenes* 130Z (SEQ ID NO: 2) |
| MSTPIITEMQ VIPVAGHDSM LLNLSGAHSP YFTRNIVILK DNSGNTGVGE VPGGEKIRQT |
| LEDAKPLVIG KTLGEYKNVM NTVRQTFNDH DAGGRGLQTF DLRTTIHVVT AIEAAMLDLL |
| GQFLGVTVAS LLGDGQQRDA VEMLGYLFFI GDRKKTTLAY QNQENDPCDW YRVRHEEAMT |
| PESVVRLAEA AYEKYGFNDF KLKGGVLDGF EEAEAVTALA KRFPDARITL DPNGAWSLDE |
| AVKIGKQLKG VLAYAEDPCG AEQGYSGREI MAEFRRATGL PTATNMIATD WRQMGHTISL |
| QSVDIPLADP HFWTMQGSIR VAQMCHEWGL TWGSHSNNHF DISLAMFTHV AAAAPGDITA |
| IDTHWIWQEG NQRLTKEPFQ IKGGLVEVPK KPGLGVELDM DQVMKANELY KSMGLGARDD |
| AMAMQFLIPG WKFDNKKPCL VR |
| Keto-deoxy-Glucarate-Dehydratase from *Acinetobacter baylyi* (ADP 1) (SEQ ID NO: 3) |
| MDALELKNIV SDGLLSFPVT DFDQNGDFNA ASYAKRLEWL APYGASALFA AGGTGEFFSL |
| TGDEYSDVIK TAVDACKGSV PIIAGAGGPT RQAILQAQEA ERLGAHGILL MPHYLTEASQ |
| EGLVEHVKQV CNAVNFGVIF YNRSVSKLNV DSLQQLVESC PNLIGFKDSS GQIDMMTEVV |
| QTLGDRLSYL GGLPTAEIFA APYKALGSPV YSSAVFNFIP KTAMEFYNAL RNDDFATTQR |
| LIRDFFLPLI KIRNRKSGYA VSMVKAGAKI VGHDAGPVRP PLSDLTPQDY EDLAALIATL |
| GPQ |
| Alcohol-Dehydrogenase YjgB from *Escherichia coli* K-12 (SEQ ID NO: 4) |
| MLYTSQTTPE KDQKMSMIKS YAAKEAGGEL EVYEYDPGEL RPQDVEVQVD YCGICHSDLS |
| MIDNEWGFSQ YPLVAGHEVI GRVVALGSAA QDKGLQVGQR VGIGWTARSC GHCDACISGN |
| QINCEQGAVP TIMNRGGFAE KLRADWQWVI PLPENIDIES AGPLLCGGIT VFKPLLMHHI |
| TATSRVGVIG IGGLGHIAIK LLHAMGCEVT AFSSNPAKEQ EVLAMGADKV VNSRDPQALK |
| ALAGQFDLII NTVNVSLDWQ PYFEALTYGG NFHTVGAVLT PLSVPAFTLI AGDRSVSGSA |
| TGTPYELRKL MRFAARSKVA PTTELFPMSK INDAIQHVRD GKARYRVVLK ADF |
| Decarboxylase from *Lactococcus lactis* IL 1403 (SEQ ID NO: 5) |
| MYTVGDYLLD RLHELGIEEI FGVPGDYNLQ FLDQIISRED MKWIGNANEL NASYMADGYA |
| RTKKAAAFLT TFGVGELSAI NGLAGSYAEN LPVVEIVGSP TSKVQNDGKF VHHTLADGDF |
| KHFMKMHEPV TAARTLLTAE NATYEIDRVL SQLLKERKPV YINLPVDVAA AKAEKPALSL |
| EKESSTTNTT EQVILSKIEE SLKNAQKPVV IAGHEVISFG LEKTVTQFVS ETKLPITTLN |

| SEQUENCES |
|---|
| FGKSAVDESL PSFLGIYNGK LSEISLKNFV ESADFILMLG VKLTDSSTGA FTHHLDENKM |
| ISLNIDEGII FNKVVEDFDF RAVVSSLSEL KGIEYEGQYI DKQYEEFIPS SAPLSQDRLW |
| QAVESLTQSN ETIVAEQGTS FFGASTIFLK SNSRFIGQPL WGSIGYTFPA ALGSQIADKE |
| SRHLLFIGDG SLQLTVQELG LSIREKLNPI CFIINNDGYT VEREIHGPTQ SYNDIPMWNY |
| SKLPETFGAT EDRVVSKIVR TENEFVSVMK EAQADVNRMY WIELVLEKED APKLLKKMGK |
| LFAEQNK |
| Alcohol-Dehydrogenase YqhD from *Escherichia coli* K-12 (SEQ ID NO: 6) |
| MNNFNLHTPT RILFGKGAIA GLREQIPHDA RVLITYGGGS VKKTGVLDQV LDALKGMDVL |
| EFGGIEPNPA YETLMNAVKL VREQKVTFLL AVGGGSVLDG TKFIAAAANY PENIDPWHIL |
| QTGGKEIKSA IPMGCVLTLP ATGSESNAGA VISRKTTGDK QAFHSAHVQP VFAVLDPVYT |
| YTLPPRQVAN GVVDAFVHTV EQYVTKPVDA KIQDRFAEGI LLTLIEDGPK ALKEPENYDV |
| RANVMWAATQ ALNGLIGAGV PQDWATHMLG HELTAMHGLD HAQTLAIVLP ALWNEKRDTK |
| RAKLLQYAER VWNITEGSDD ERIDAAIAAT RNFFEQLGVP HLSDYGLDG SSIPALLKKL |
| EEHGMTQLGE NHDITLDVSR RIYEAAR |

The invention claimed is:

1. A process for producing an alcohol of formula (I) or an amine of formula (II):

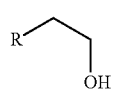
(I)

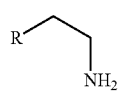
(II)

from a substrate of the formula (III) and/or (IV)

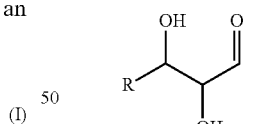
(III)

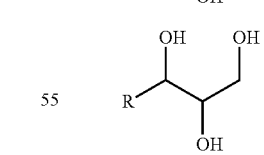
(IV)

wherein the process comprises the following reactions:
(a) oxidation of at least one terminal C-atom
(b) dehydration
(c) decarboxylation
(d) reduction in case of the product of the formula (I) and amination in the case of the product of the formula (II);
wherein at least reaction b is enzyme-catalyzed and R is a $C_{1-20}$ alkyl, wherein the alkyl may be substituted with one or more hydroxyl groups; and wherein the process is catalyzed by less than 10 enzymes; and wherein the process is performed in a single reaction vessel or in more than one reaction vessel.

2. The process of claim 1, wherein R is —CH$_2$OH, —CH(OH)—CH$_2$(OH) or —CH(OH)—CH(OH)—CH$_2$(OH).

3. The process of claim 1, wherein the substrate is a C$_6$-polyol, C$_6$-sugar or C$_6$-sugar acid.

4. The process of claim 1, wherein the alcohol of formula (I) is 1,4 butanediol or wherein the amine of formula (II) is 1,4-diaminobutane.

5. The process of claim 1, wherein each of the steps a-d is enzyme-catalyzed.

6. The process of claim 5, wherein the process is carried out in a microbial cell, which recombinantly expresses the enzymes.

7. The process of claim 1, wherein reaction a is catalyzed by an oxidoreductase, reaction b is catalyzed by a dehydratase, reaction c is catalyzed by a decarboxylase and reaction d is catalyzed by an aminotransferase or an oxidoreductase.

8. The process of claim 7, wherein the oxidoreductase is an alcohol dehydrogenase, aldehyde dehydrogenase, amino acid dehydrogenase, alcohol oxidase and/or aldehyde oxidase.

9. The process of claim 1, wherein the process is performed in the presence of one or more cofactors for transfer of reduction equivalents.

10. The process of claim 9, wherein one cofactor is NAD$^+$/NADH.

11. The process of claim 1, wherein the process is carried out in a cell-free in vitro system.

12. The process of claim 1, wherein the process is performed in a bioreactor.

13. The process of claim 1, wherein the process produces a bifunctional C4 molecule from a C6 substrate, and wherein the bond between the C3 and the C4 is left intact.

14. The process of claim 13, wherein the bifunctional C4 molecule is 1,4-butanediol.

15. The process of claim 13, wherein the C6 substrate is hexose.

* * * * *

SEQUENCE LISTING

<160> NUMBER OF SEQ ID NOS: 6

<210> SEQ ID NO 1
<211> LENGTH: 265
<212> TYPE: PRT
<213> ORGANISM: Agrobacterium tumefaciens

<400> SEQUENCE: 1

Met Lys Arg Leu Leu Val Thr Gly Ala Ala Gly Gln Leu Gly Arg Val
1               5                   10                  15

Met Arg Glu Arg Leu Ala Pro Met Ala Glu Ile Leu Arg Leu Ala Asp
            20                  25                  30

Leu Ser Pro Leu Asp Pro Ala Gly Pro Asn Glu Glu Cys Val Gln Cys
        35                  40                  45

Asp Leu Ala Asp Ala Asn Ala Val Asn Ala Met Val Ala Gly Cys Asp
    50                  55                  60

Gly Ile Val His Leu Gly Gly Ile Ser Val Glu Lys Pro Phe Glu Gln
65                  70                  75                  80

Ile Leu Gln Gly Asn Ile Ile Gly Leu Tyr Asn Leu Tyr Glu Ala Ala
                85                  90                  95

Arg Ala His Gly Gln Pro Arg Ile Val Phe Ala Ser Ser Asn His Thr
            100                 105                 110

Ile Gly Tyr Tyr Pro Gln Thr Glu Arg Leu Gly Pro Asp Val Pro Ala
        115                 120                 125

Arg Pro Asp Gly Leu Tyr Gly Val Ser Lys Cys Phe Gly Glu Asn Leu
130                 135                 140

Ala Arg Met Tyr Phe Asp Lys Phe Gly Gln Glu Thr Ala Leu Val Arg
145                 150                 155                 160

Ile Gly Ser Cys Thr Pro Glu Pro Asn Asn Tyr Arg Met Leu Ser Thr
                165                 170                 175

Trp Phe Ser His Asp Asp Phe Val Ser Leu Ile Glu Ala Val Phe Arg

```
                180                 185                 190
Ala Pro Val Leu Gly Cys Pro Val Trp Gly Ala Ser Ala Asn Asp
            195                 200                 205

Ala Gly Trp Trp Asp Asn Ser His Leu Gly Phe Leu Gly Trp Lys Pro
        210                 215                 220

Lys Asp Asn Ala Glu Ala Phe Arg Arg His Ile Thr Glu Thr Thr Pro
225                 230                 235                 240

Pro Pro Asp Pro Asn Asp Ala Leu Val Arg Phe Gln Gly Gly Thr Phe
            245                 250                 255

Val Asp Asn Pro Ile Phe Lys Gln Ser
        260                 265

<210> SEQ ID NO 2
<211> LENGTH: 442
<212> TYPE: PRT
<213> ORGANISM: Actinobacillus succinogenes

<400> SEQUENCE: 2

Met Ser Thr Pro Ile Ile Thr Glu Met Gln Val Ile Pro Val Ala Gly
1               5                   10                  15

His Asp Ser Met Leu Leu Asn Leu Ser Gly Ala His Ser Pro Tyr Phe
            20                  25                  30

Thr Arg Asn Ile Val Ile Leu Lys Asp Asn Ser Gly Asn Thr Gly Val
        35                  40                  45

Gly Glu Val Pro Gly Gly Glu Lys Ile Arg Gln Thr Leu Glu Asp Ala
    50                  55                  60

Lys Pro Leu Val Ile Gly Lys Thr Leu Gly Glu Tyr Lys Asn Val Met
65                  70                  75                  80

Asn Thr Val Arg Gln Thr Phe Asn Asp His Asp Ala Gly Gly Arg Gly
            85                  90                  95

Leu Gln Thr Phe Asp Leu Arg Thr Thr Ile His Val Val Thr Ala Ile
        100                 105                 110

Glu Ala Ala Met Leu Asp Leu Leu Gly Gln Phe Leu Gly Val Thr Val
    115                 120                 125

Ala Ser Leu Leu Gly Asp Gly Gln Gln Arg Asp Ala Val Glu Met Leu
130                 135                 140

Gly Tyr Leu Phe Phe Ile Gly Asp Arg Lys Lys Thr Thr Leu Ala Tyr
145                 150                 155                 160

Gln Asn Gln Glu Asn Asp Pro Cys Asp Trp Tyr Arg Val Arg His Glu
            165                 170                 175

Glu Ala Met Thr Pro Glu Ser Val Val Arg Leu Ala Glu Ala Ala Tyr
        180                 185                 190

Glu Lys Tyr Gly Phe Asn Asp Phe Lys Leu Lys Gly Gly Val Leu Asp
    195                 200                 205

Gly Phe Glu Glu Ala Glu Ala Val Thr Ala Leu Ala Lys Arg Phe Pro
210                 215                 220

Asp Ala Arg Ile Thr Leu Asp Pro Asn Gly Ala Trp Ser Leu Asp Glu
225                 230                 235                 240

Ala Val Lys Ile Gly Lys Gln Leu Lys Gly Val Leu Ala Tyr Ala Glu
            245                 250                 255

Asp Pro Cys Gly Ala Glu Gln Gly Tyr Ser Gly Arg Glu Ile Met Ala
        260                 265                 270

Glu Phe Arg Arg Ala Thr Gly Leu Pro Thr Ala Thr Asn Met Ile Ala
    275                 280                 285
```

```
Thr Asp Trp Arg Gln Met Gly His Thr Ile Ser Leu Gln Ser Val Asp
            290                 295                 300
Ile Pro Leu Ala Asp Pro His Phe Trp Thr Met Gln Gly Ser Ile Arg
305                 310                 315                 320
Val Ala Gln Met Cys His Glu Trp Gly Leu Thr Trp Gly Ser His Ser
                325                 330                 335
Asn Asn His Phe Asp Ile Ser Leu Ala Met Phe Thr His Val Ala Ala
            340                 345                 350
Ala Ala Pro Gly Asp Ile Thr Ala Ile Asp Thr His Trp Ile Trp Gln
            355                 360                 365
Glu Gly Asn Gln Arg Leu Thr Lys Glu Pro Phe Gln Ile Lys Gly Gly
    370                 375                 380
Leu Val Glu Val Pro Lys Lys Pro Gly Leu Gly Val Glu Leu Asp Met
385                 390                 395                 400
Asp Gln Val Met Lys Ala Asn Glu Leu Tyr Lys Ser Met Gly Leu Gly
                405                 410                 415
Ala Arg Asp Asp Ala Met Ala Met Gln Phe Leu Ile Pro Gly Trp Lys
                420                 425                 430
Phe Asp Asn Lys Lys Pro Cys Leu Val Arg
            435                 440

<210> SEQ ID NO 3
<211> LENGTH: 303
<212> TYPE: PRT
<213> ORGANISM: Acinetobacter baylyi

<400> SEQUENCE: 3

Met Asp Ala Leu Glu Leu Lys Asn Ile Val Ser Asp Gly Leu Leu Ser
1               5                   10                  15
Phe Pro Val Thr Asp Phe Asp Gln Asn Gly Asp Phe Asn Ala Ala Ser
                20                  25                  30
Tyr Ala Lys Arg Leu Glu Trp Leu Ala Pro Tyr Gly Ala Ser Ala Leu
            35                  40                  45
Phe Ala Ala Gly Gly Thr Gly Glu Phe Phe Ser Leu Thr Gly Asp Glu
    50                  55                  60
Tyr Ser Asp Val Ile Lys Thr Ala Val Asp Ala Cys Lys Gly Ser Val
65                  70                  75                  80
Pro Ile Ile Ala Gly Ala Gly Gly Pro Thr Arg Gln Ala Ile Leu Gln
                85                  90                  95
Ala Gln Glu Ala Glu Arg Leu Gly Ala His Gly Ile Leu Leu Met Pro
            100                 105                 110
His Tyr Leu Thr Glu Ala Ser Gln Glu Gly Leu Val Glu His Val Lys
        115                 120                 125
Gln Val Cys Asn Ala Val Asn Phe Gly Val Ile Phe Tyr Asn Arg Ser
    130                 135                 140
Val Ser Lys Leu Asn Val Asp Ser Leu Gln Gln Leu Val Glu Ser Cys
145                 150                 155                 160
Pro Asn Leu Ile Gly Phe Lys Asp Ser Ser Gly Gln Ile Asp Met Met
                165                 170                 175
Thr Glu Val Val Gln Thr Leu Gly Asp Arg Leu Ser Tyr Leu Gly Gly
            180                 185                 190
Leu Pro Thr Ala Glu Ile Phe Ala Ala Pro Tyr Lys Ala Leu Gly Ser
        195                 200                 205
Pro Val Tyr Ser Ser Ala Val Phe Asn Phe Ile Pro Lys Thr Ala Met
    210                 215                 220
```

```
Glu Phe Tyr Asn Ala Leu Arg Asn Asp Asp Phe Ala Thr Thr Gln Arg
225                 230                 235                 240

Leu Ile Arg Asp Phe Phe Leu Pro Leu Ile Lys Ile Arg Asn Arg Lys
                245                 250                 255

Ser Gly Tyr Ala Val Ser Met Val Lys Ala Gly Ala Lys Ile Val Gly
            260                 265                 270

His Asp Ala Gly Pro Val Arg Pro Pro Leu Ser Asp Leu Thr Pro Gln
        275                 280                 285

Asp Tyr Glu Asp Leu Ala Ala Leu Ile Ala Thr Leu Gly Pro Gln
290                 295                 300

<210> SEQ ID NO 4
<211> LENGTH: 353
<212> TYPE: PRT
<213> ORGANISM: Escherichia coli

<400> SEQUENCE: 4

Met Leu Tyr Thr Ser Gln Thr Thr Pro Glu Lys Asp Gln Lys Met Ser
1               5                   10                  15

Met Ile Lys Ser Tyr Ala Ala Lys Glu Ala Gly Gly Glu Leu Glu Val
            20                  25                  30

Tyr Glu Tyr Asp Pro Gly Glu Leu Arg Pro Gln Asp Val Glu Val Gln
        35                  40                  45

Val Asp Tyr Cys Gly Ile Cys His Ser Asp Leu Ser Met Ile Asp Asn
50                  55                  60

Glu Trp Gly Phe Ser Gln Tyr Pro Leu Val Ala Gly His Glu Val Ile
65                  70                  75                  80

Gly Arg Val Val Ala Leu Gly Ser Ala Ala Gln Asp Lys Gly Leu Gln
                85                  90                  95

Val Gly Gln Arg Val Gly Ile Gly Trp Thr Ala Arg Ser Cys Gly His
            100                 105                 110

Cys Asp Ala Cys Ile Ser Gly Asn Gln Ile Asn Cys Glu Gln Gly Ala
        115                 120                 125

Val Pro Thr Ile Met Asn Arg Gly Gly Phe Ala Glu Lys Leu Arg Ala
130                 135                 140

Asp Trp Gln Trp Val Ile Pro Leu Pro Glu Asn Ile Asp Ile Glu Ser
145                 150                 155                 160

Ala Gly Pro Leu Leu Cys Gly Gly Ile Thr Val Phe Lys Pro Leu Leu
                165                 170                 175

Met His His Ile Thr Ala Thr Ser Arg Val Gly Val Ile Gly Ile Gly
            180                 185                 190

Gly Leu Gly His Ile Ala Ile Lys Leu Leu His Ala Met Gly Cys Glu
        195                 200                 205

Val Thr Ala Phe Ser Ser Asn Pro Ala Lys Glu Gln Glu Val Leu Ala
210                 215                 220

Met Gly Ala Asp Lys Val Val Asn Ser Arg Asp Pro Gln Ala Leu Lys
225                 230                 235                 240

Ala Leu Ala Gly Gln Phe Asp Leu Ile Ile Asn Thr Val Asn Val Ser
                245                 250                 255

Leu Asp Trp Gln Pro Tyr Phe Glu Ala Leu Thr Tyr Gly Gly Asn Phe
            260                 265                 270

His Thr Val Gly Ala Val Leu Thr Pro Leu Ser Val Pro Ala Phe Thr
        275                 280                 285

Leu Ile Ala Gly Asp Arg Ser Val Ser Gly Ser Ala Thr Gly Thr Pro
```

```
            290                 295                 300
Tyr Glu Leu Arg Lys Leu Met Arg Phe Ala Ala Arg Ser Lys Val Ala
305                 310                 315                 320

Pro Thr Thr Glu Leu Phe Pro Met Ser Lys Ile Asn Asp Ala Ile Gln
                325                 330                 335

His Val Arg Asp Gly Lys Ala Arg Tyr Arg Val Val Leu Lys Ala Asp
            340                 345                 350

Phe

<210> SEQ ID NO 5
<211> LENGTH: 547
<212> TYPE: PRT
<213> ORGANISM: Lactococcus lactis

<400> SEQUENCE: 5

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
```

```
            305                 310                 315                 320
Arg Ala Val Val Ser Ser Leu Ser Glu Leu Lys Gly Ile Glu Tyr Glu
                    325                 330                 335

Gly Gln Tyr Ile Asp Lys Gln Tyr Glu Glu Phe Ile Pro Ser Ser Ala
                340                 345                 350

Pro Leu Ser Gln Asp Arg Leu Trp Gln Ala Val Glu Ser Leu Thr Gln
            355                 360                 365

Ser Asn Glu Thr Ile Val Ala Glu Gln Gly Thr Ser Phe Phe Gly Ala
        370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Met Gly Lys Leu Phe Ala Glu
    530                 535                 540

Gln Asn Lys
545

<210> SEQ ID NO 6
<211> LENGTH: 386
<212> TYPE: PRT
<213> ORGANISM: Escherichia coli

<400> SEQUENCE: 6

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
        50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125
```

```
Ser Ala Ile Pro Met Gly Cys Val Leu Thr Leu Pro Ala Thr Gly Ser
    130             135                 140
Glu Ser Asn Ala Gly Ala Val Ile Ser Arg Lys Thr Thr Gly Asp Lys
145             150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
            180                 185                 190
Val Asp Ala Phe Val His Thr Val Glu Gln Tyr Val Thr Lys Pro Val
        195                 200                 205
Asp Ala Lys Ile Gln Asp Arg Phe Ala Glu Gly Ile Leu Leu Thr Leu
    210                 215                 220
Ile Glu Asp Gly Pro Lys Ala Leu Lys Glu Pro Glu Asn Tyr Asp Val
225             230                 235                 240
Arg Ala Asn Val Met Trp Ala Ala Thr Gln Ala Leu Asn Gly Leu Ile
                245                 250                 255
Gly Ala Gly Val Pro Gln Asp Trp Ala Thr His Met Leu Gly His Glu
            260                 265                 270
Leu Thr Ala Met His Gly Leu Asp His Ala Gln Thr Leu Ala Ile Val
        275                 280                 285
Leu Pro Ala Leu Trp Asn Glu Lys Arg Asp Thr Lys Arg Ala Lys Leu
    290                 295                 300
Leu Gln Tyr Ala Glu Arg Val Trp Asn Ile Thr Glu Gly Ser Asp Asp
305             310                 315                 320
Glu Arg Ile Asp Ala Ala Ile Ala Ala Thr Arg Asn Phe Phe Glu Gln
                325                 330                 335
Leu Gly Val Pro His Leu Ser Asp Tyr Gly Leu Asp Gly Ser Ser Ile
            340                 345                 350
Pro Ala Leu Leu Lys Lys Leu Glu Glu His Gly Met Thr Gln Leu Gly
        355                 360                 365
Glu Asn His Asp Ile Thr Leu Asp Val Ser Arg Arg Ile Tyr Glu Ala
    370                 375                 380
Ala Arg
385
```